United States Patent
Voegele et al.

(10) Patent No.: US 10,092,291 B2
(45) Date of Patent: Oct. 9, 2018

(54) SURGICAL INSTRUMENT WITH SELECTIVELY RIGIDIZABLE FEATURES

(75) Inventors: James W. Voegele, Cincinnati, OH (US); Aaron C. Voegele, Loveland, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 357 days.

(21) Appl. No.: 13/013,147

(22) Filed: Jan. 25, 2011

(65) Prior Publication Data

US 2012/0191076 A1     Jul. 26, 2012

(51) Int. Cl.
*A61B 17/00* (2006.01)
*A61M 25/00* (2006.01)
(Continued)

(52) U.S. Cl.
CPC .... *A61B 17/07207* (2013.01); *A61B 17/1152* (2013.01); *A61B 17/34* (2013.01);
(Continued)

(58) Field of Classification Search
CPC ........... A61B 2017/00862; A61B 2017/00867; A61M 25/0054; A61M 2205/0266; A61M 2025/0064
See application file for complete search history.

(56) References Cited

U.S. PATENT DOCUMENTS

| | | |
|---|---|---|
| 645,576 A | 3/1900 | Tesla |
| 649,621 A | 5/1900 | Tesla |

(Continued)

FOREIGN PATENT DOCUMENTS

| | | |
|---|---|---|
| AU | 666310 B2 | 2/1996 |
| DE | 3008120 A1 | 9/1980 |

(Continued)

OTHER PUBLICATIONS

Michael S. Kavic, M.D., "Natural Orifice Translumenal Endoscopic Surgery: "Notes"", JSLA, vol. 10, pp. 133-134 (2006).

(Continued)

*Primary Examiner* — Scott T Luan

(57) ABSTRACT

Mechanisms for altering the shape of a cell or chamber of a shaft or an actuation drive of an instrument are provided. The mechanisms may selectively rigidize the shaft of surgical or diagnostic instruments. The shaft assembly includes a shaft operatively connectable to a control member, at least one cell or a set of cells defined within the shaft, a shape altering material contained within the cell or cells, and, an activation link operatively connectable to a source of activation energy for delivering activation energy to each cell for activating the shape altering material to selectively rigidize or unrigidize the shaft. An actuator for producing work is also provided that includes an element within a housing that defines a cell or a set of cells. The shape altering material is contained within the cells, and a source of activation energy operatively connected to each cell for activating the shape altering material to expand or contract the cell. The element is operatively connectable to a driving member of an instrument such that the change in the cell is translated to the driving member to facilitate the production of work.

5 Claims, 11 Drawing Sheets

(51) Int. Cl.
*A61B 17/072* (2006.01)
*A61B 17/115* (2006.01)
*A61B 17/34* (2006.01)

(52) U.S. Cl.
CPC ............... *A61B 2017/003* (2013.01); *A61B 2017/00539* (2013.01); *A61B 2017/00862* (2013.01)

(56) References Cited

U.S. PATENT DOCUMENTS

| | | | |
|---|---|---|---|
| 787,412 A | 4/1905 | Tesla | |
| 1,039,354 A | 9/1912 | Bonadio | |
| 1,127,948 A | 2/1915 | Wappler | |
| 1,482,653 A | 2/1924 | Lilly | |
| 1,625,602 A | 4/1927 | Gould et al. | |
| 1,916,722 A | 7/1933 | Ende | |
| 2,028,635 A | 1/1936 | Wappler | |
| 2,031,682 A | 2/1936 | Wappler et al. | |
| 2,113,246 A | 4/1938 | Wappler | |
| 2,155,365 A | 4/1939 | Rankin | |
| 2,191,858 A | 2/1940 | Moore | |
| 2,196,620 A | 4/1940 | Attarian | |
| 2,388,137 A | 10/1945 | Graumlich | |
| 2,493,108 A | 1/1950 | Casey, Jr. | |
| 2,504,152 A | 4/1950 | Riker et al. | |
| 2,938,382 A | 5/1960 | De Graaf | |
| 2,952,206 A | 9/1960 | Becksted | |
| 3,069,195 A | 12/1962 | Buck | |
| 3,070,088 A | 12/1962 | Brahos | |
| 3,170,471 A | 2/1965 | Schnitzer | |
| 3,435,824 A | 4/1969 | Gamponia | |
| 3,470,876 A | 10/1969 | Barchilon | |
| 3,595,239 A | 7/1971 | Petersen | |
| 3,669,487 A | 6/1972 | Roberts et al. | |
| 3,746,881 A | 7/1973 | Fitch et al. | |
| 3,799,672 A | 3/1974 | Vurek | |
| 3,854,473 A | 12/1974 | Matsuo | |
| 3,946,740 A | 3/1976 | Bassett | |
| 3,948,251 A | 4/1976 | Hosono | |
| 3,961,632 A | 6/1976 | Moossun | |
| 3,965,890 A | 6/1976 | Gauthier | |
| 3,994,301 A | 11/1976 | Agris | |
| 4,011,872 A | 3/1977 | Komiya | |
| 4,012,812 A | 3/1977 | Black | |
| 4,085,743 A | 4/1978 | Yoon | |
| 4,164,225 A | 8/1979 | Johnson et al. | |
| 4,174,715 A | 11/1979 | Hasson | |
| 4,178,920 A | 12/1979 | Cawood, Jr. et al. | |
| 4,207,873 A | 6/1980 | Kruy | |
| 4,235,238 A | 11/1980 | Ogiu et al. | |
| 4,258,716 A | 3/1981 | Sutherland | |
| 4,269,174 A | 5/1981 | Adair | |
| 4,278,077 A | 7/1981 | Mizumoto | |
| 4,285,344 A | 8/1981 | Marshall | |
| 4,311,143 A | 1/1982 | Komiya | |
| 4,329,980 A | 5/1982 | Terada | |
| 4,396,021 A | 8/1983 | Baumgartner | |
| 4,406,656 A | 9/1983 | Nattier et al. | |
| 4,452,246 A | 6/1984 | Bader et al. | |
| 4,461,281 A | 7/1984 | Carson | |
| 4,491,132 A | 1/1985 | Aikins | |
| 4,527,331 A | 7/1985 | Lasner et al. | |
| 4,527,564 A | 7/1985 | Eguchi et al. | |
| 4,538,594 A | 9/1985 | Boebel et al. | |
| D281,104 S | 10/1985 | Davison | |
| 4,569,347 A | 2/1986 | Frisbie | |
| 4,580,551 A | 4/1986 | Siegmund et al. | |
| 4,646,722 A | 3/1987 | Silverstein et al. | |
| 4,653,476 A | 3/1987 | Bonnet | |
| 4,655,219 A | 4/1987 | Petruzzi | |
| 4,669,470 A | 6/1987 | Brandfield | |
| 4,671,477 A | 6/1987 | Cullen | |
| 4,677,982 A | 7/1987 | Llinas et al. | |
| 4,685,447 A | 8/1987 | Iversen et al. | |
| 4,711,240 A | 12/1987 | Goldwasser et al. | |
| 4,712,545 A | 12/1987 | Honkanen | |
| 4,721,116 A | 1/1988 | Schintgen et al. | |
| 4,727,600 A | 2/1988 | Avakian | |
| 4,733,662 A | 3/1988 | DeSatnick et al. | |
| D295,894 S | 5/1988 | Sharkany et al. | |
| 4,753,223 A * | 6/1988 | Bremer ..................... 600/140 |
| 4,763,669 A | 8/1988 | Jaeger | |
| 4,770,188 A | 9/1988 | Chikama | |
| 4,790,624 A * | 12/1988 | Van Hoye et al. ........... 385/118 |
| 4,815,450 A | 3/1989 | Patel | |
| 4,823,794 A | 4/1989 | Pierce | |
| 4,829,999 A | 5/1989 | Auth | |
| 4,867,140 A | 9/1989 | Hovis et al. | |
| 4,869,238 A | 9/1989 | Opie et al. | |
| 4,869,459 A | 9/1989 | Bourne | |
| 4,873,979 A | 10/1989 | Hanna | |
| 4,880,015 A | 11/1989 | Nierman | |
| 4,911,148 A | 3/1990 | Sosnowski et al. | |
| 4,926,860 A | 5/1990 | Stice et al. | |
| 4,938,214 A | 7/1990 | Specht et al. | |
| 4,950,273 A | 8/1990 | Briggs | |
| 4,950,285 A | 8/1990 | Wilk | |
| 4,953,539 A | 9/1990 | Nakamura et al. | |
| 4,960,133 A | 10/1990 | Hewson | |
| 4,977,887 A | 12/1990 | Gouda | |
| 4,979,950 A | 12/1990 | Transue et al. | |
| 4,984,581 A | 1/1991 | Stice | |
| 4,994,079 A | 2/1991 | Genese et al. | |
| 5,007,917 A | 4/1991 | Evans | |
| 5,010,876 A | 4/1991 | Henley et al. | |
| 5,020,514 A | 6/1991 | Heckele | |
| 5,020,535 A | 6/1991 | Parker et al. | |
| 5,025,778 A | 6/1991 | Silverstein et al. | |
| 5,033,169 A | 7/1991 | Bindon | |
| 5,037,433 A | 8/1991 | Wilk et al. | |
| 5,041,129 A | 8/1991 | Hayhurst et al. | |
| 5,046,513 A | 9/1991 | Gatturna et al. | |
| 5,050,585 A | 9/1991 | Takahashi | |
| 5,052,372 A | 10/1991 | Shapiro | |
| 5,065,516 A | 11/1991 | Dulebohn | |
| 5,066,295 A | 11/1991 | Kozak et al. | |
| 5,108,421 A | 4/1992 | Fowler | |
| 5,123,913 A | 6/1992 | Wilk et al. | |
| 5,123,914 A | 6/1992 | Cope | |
| 5,133,727 A | 7/1992 | Bales et al. | |
| 5,147,374 A | 9/1992 | Fernandez | |
| 5,174,300 A | 12/1992 | Bales et al. | |
| 5,176,126 A | 1/1993 | Chikama | |
| 5,190,050 A | 3/1993 | Nitzsche | |
| 5,190,555 A | 3/1993 | Wetter et al. | |
| 5,192,284 A | 3/1993 | Pleatman | |
| 5,192,300 A | 3/1993 | Fowler | |
| 5,197,963 A | 3/1993 | Parins | |
| 5,201,752 A | 4/1993 | Brown et al. | |
| 5,201,908 A | 4/1993 | Jones | |
| 5,203,785 A | 4/1993 | Slater | |
| 5,203,787 S | 4/1993 | Noblitt et al. | |
| 5,209,747 A | 5/1993 | Knoepfler | |
| 5,217,003 A | 6/1993 | Wilk | |
| 5,217,453 A | 6/1993 | Wilk | |
| 5,219,357 A | 6/1993 | Honkanen et al. | |
| 5,219,358 A | 6/1993 | Bendel et al. | |
| 5,222,362 A | 6/1993 | Maus et al. | |
| 5,222,965 A | 6/1993 | Haughton | |
| 5,234,437 A | 8/1993 | Sepetka | |
| 5,234,453 A | 8/1993 | Smith et al. | |
| 5,235,964 A | 8/1993 | Abenaim | |
| 5,242,456 A | 9/1993 | Nash et al. | |
| 5,245,460 A | 9/1993 | Allen et al. | |
| 5,246,424 A | 9/1993 | Wilk | |
| 5,257,999 A | 11/1993 | Slanetz, Jr. | |
| 5,259,366 A | 11/1993 | Reydel | |
| 5,263,958 A | 11/1993 | deGuillebon et al. | |
| 5,273,524 A | 12/1993 | Fox et al. | |
| 5,275,607 A | 1/1994 | Lo et al. | |
| 5,275,614 A | 1/1994 | Haber et al. | |
| 5,275,616 A | 1/1994 | Fowler | |
| 5,284,128 A | 2/1994 | Hart | |

(56) References Cited

U.S. PATENT DOCUMENTS

| | | |
|---|---|---|
| 5,284,162 A | 2/1994 | Wilk |
| 5,287,845 A | 2/1994 | Faul et al. |
| 5,287,852 A | 2/1994 | Arkinstall |
| 5,290,299 A | 3/1994 | Fain et al. |
| 5,290,302 A | 3/1994 | Pericic |
| 5,295,977 A | 3/1994 | Cohen et al. |
| 5,297,536 A | 3/1994 | Wilk |
| 5,297,687 A | 3/1994 | Freed |
| 5,301,061 A | 4/1994 | Nakada et al. |
| 5,312,023 A | 5/1994 | Green et al. |
| 5,312,333 A | 5/1994 | Churinetz et al. |
| 5,312,351 A | 5/1994 | Gerrone |
| 5,312,416 A | 5/1994 | Spaeth et al. |
| 5,312,423 A | 5/1994 | Rosenbluth et al. |
| 5,318,589 A | 6/1994 | Lichtman |
| 5,320,636 A | 6/1994 | Slater |
| 5,324,261 A | 6/1994 | Amundson et al. |
| 5,325,845 A | 7/1994 | Adair |
| 5,330,471 A | 7/1994 | Eggers |
| 5,330,486 A | 7/1994 | Wilk |
| 5,330,488 A | 7/1994 | Goldrath |
| 5,330,496 A | 7/1994 | Alferness |
| 5,330,502 A | 7/1994 | Hassler et al. |
| 5,331,971 A | 7/1994 | Bales et al. |
| 5,334,168 A * | 8/1994 | Hemmer ............... 604/531 |
| 5,334,198 A | 8/1994 | Hart et al. |
| 5,341,815 A | 8/1994 | Cofone et al. |
| 5,342,396 A | 8/1994 | Cook |
| 5,344,428 A | 9/1994 | Griffiths |
| 5,345,927 A | 9/1994 | Bonutti |
| 5,350,391 A | 9/1994 | Iacovelli |
| 5,352,184 A | 10/1994 | Goldberg et al. |
| 5,352,222 A | 10/1994 | Rydell |
| 5,354,302 A | 10/1994 | Ko |
| 5,354,311 A | 10/1994 | Kambin et al. |
| 5,356,381 A | 10/1994 | Ensminger et al. |
| 5,356,408 A | 10/1994 | Rydell |
| 5,360,428 A | 11/1994 | Hutchinson, Jr. |
| 5,364,408 A | 11/1994 | Gordon |
| 5,364,410 A | 11/1994 | Failla et al. |
| 5,366,466 A | 11/1994 | Christian et al. |
| 5,366,467 A | 11/1994 | Lynch et al. |
| 5,368,605 A | 11/1994 | Miller, Jr. |
| 5,370,647 A | 12/1994 | Graber et al. |
| 5,370,679 A | 12/1994 | Atlee |
| 5,374,273 A | 12/1994 | Nakao et al. |
| 5,374,275 A | 12/1994 | Bradley et al. |
| 5,374,277 A | 12/1994 | Hassler |
| 5,377,695 A | 1/1995 | An Haack |
| 5,383,877 A | 1/1995 | Clarke |
| 5,383,888 A | 1/1995 | Zvenyatsky et al. |
| 5,386,817 A | 2/1995 | Jones |
| 5,387,259 A | 2/1995 | Davidson |
| 5,391,174 A | 2/1995 | Weston |
| 5,392,789 A | 2/1995 | Slater et al. |
| 5,395,386 A | 3/1995 | Slater |
| 5,401,248 A | 3/1995 | Bencini |
| 5,403,311 A | 4/1995 | Abele et al. |
| 5,403,328 A | 4/1995 | Shallman |
| 5,403,342 A | 4/1995 | Tovey et al. |
| 5,403,348 A | 4/1995 | Bonutti |
| 5,405,073 A | 4/1995 | Porter |
| 5,405,359 A | 4/1995 | Pierce |
| 5,409,478 A | 4/1995 | Gerry et al. |
| 5,417,699 A | 5/1995 | Klein et al. |
| 5,423,821 A | 6/1995 | Pasque |
| 5,433,721 A | 7/1995 | Hooven et al. |
| 5,439,471 A | 8/1995 | Kerr |
| 5,439,478 A | 8/1995 | Palmer |
| 5,441,059 A | 8/1995 | Dannan |
| 5,441,494 A | 8/1995 | Ortiz |
| 5,441,499 A | 8/1995 | Fritzsch |
| 5,443,463 A | 8/1995 | Stern et al. |
| 5,445,638 A | 8/1995 | Rydell et al. |
| 5,445,648 A | 8/1995 | Cook |
| 5,449,021 A | 9/1995 | Chikama |
| 5,454,827 A | 10/1995 | Aust et al. |
| 5,456,667 A | 10/1995 | Ham et al. |
| 5,456,684 A | 10/1995 | Schmidt et al. |
| 5,458,131 A | 10/1995 | Wilk |
| 5,458,583 A | 10/1995 | McNeely et al. |
| 5,460,168 A | 10/1995 | Masubuchi et al. |
| 5,460,629 A | 10/1995 | Shlain et al. |
| 5,462,561 A | 10/1995 | Voda |
| 5,465,731 A | 11/1995 | Bell et al. |
| 5,467,763 A | 11/1995 | McMahon et al. |
| 5,468,250 A | 11/1995 | Paraschac et al. |
| 5,470,308 A | 11/1995 | Edwards et al. |
| 5,470,320 A | 11/1995 | Tiefenbrun et al. |
| 5,478,347 A | 12/1995 | Aranyi |
| 5,478,352 A | 12/1995 | Fowler |
| 5,480,404 A | 1/1996 | Kammerer et al. |
| 5,482,029 A * | 1/1996 | Sekiguchi et al. ............ 600/109 |
| 5,482,054 A | 1/1996 | Slater et al. |
| 5,484,451 A | 1/1996 | Akopov et al. |
| 5,489,256 A | 2/1996 | Adair |
| 5,496,347 A | 3/1996 | Hashiguchi et al. |
| 5,499,990 A | 3/1996 | Schülken et al. |
| 5,499,992 A | 3/1996 | Meade et al. |
| 5,501,692 A | 3/1996 | Riza |
| 5,503,616 A | 4/1996 | Jones |
| 5,505,686 A | 4/1996 | Willis et al. |
| 5,507,755 A | 4/1996 | Gresl et al. |
| 5,511,564 A | 4/1996 | Wilk |
| 5,514,157 A | 5/1996 | Nicholas et al. |
| 5,518,501 A | 5/1996 | Oneda et al. |
| 5,522,829 A | 6/1996 | Michalos |
| 5,522,830 A | 6/1996 | Aranyi |
| 5,527,321 A | 6/1996 | Hinchliffe |
| 5,533,418 A | 7/1996 | Wu et al. |
| 5,536,248 A | 7/1996 | Weaver et al. |
| 5,538,509 A | 7/1996 | Dunlap et al. |
| 5,540,648 A | 7/1996 | Yoon |
| 5,549,637 A | 8/1996 | Crainich |
| 5,554,151 A | 9/1996 | Hinchliffe |
| 5,555,883 A | 9/1996 | Avitall |
| 5,558,133 A | 9/1996 | Bortoli et al. |
| 5,562,693 A | 10/1996 | Devlin et al. |
| 5,569,243 A | 10/1996 | Kortenbach et al. |
| 5,569,298 A | 10/1996 | Schnell |
| 5,571,090 A | 11/1996 | Sherts |
| 5,573,540 A | 11/1996 | Yoon |
| 5,578,030 A | 11/1996 | Levin |
| 5,582,611 A | 12/1996 | Tsuruta et al. |
| 5,582,617 A | 12/1996 | Klieman et al. |
| 5,584,845 A | 12/1996 | Hart |
| 5,591,179 A | 1/1997 | Edelstein |
| 5,591,205 A | 1/1997 | Fowler |
| 5,593,420 A | 1/1997 | Eubanks, Jr. et al. |
| 5,595,562 A | 1/1997 | Grier |
| 5,597,378 A | 1/1997 | Jervis |
| 5,601,573 A | 2/1997 | Fogelberg et al. |
| 5,601,588 A | 2/1997 | Tonomura et al. |
| 5,601,602 A | 2/1997 | Fowler |
| 5,604,531 A | 2/1997 | Iddan et al. |
| 5,607,389 A | 3/1997 | Edwards et al. |
| 5,607,406 A | 3/1997 | Hernandez et al. |
| 5,607,450 A | 3/1997 | Zvenyatsky et al. |
| 5,609,601 A | 3/1997 | Kolesa et al. |
| 5,613,975 A | 3/1997 | Christy |
| 5,616,117 A | 4/1997 | Dinkier et al. |
| 5,618,303 A | 4/1997 | Marlow et al. |
| 5,620,415 A | 4/1997 | Lucey et al. |
| 5,624,399 A | 4/1997 | Ackerman |
| 5,624,431 A | 4/1997 | Gerry et al. |
| 5,626,578 A | 5/1997 | Tihon |
| 5,628,732 A | 5/1997 | Antoon, Jr. et al. |
| 5,630,782 A | 5/1997 | Adair |
| 5,643,283 A | 7/1997 | Younker |
| 5,643,292 A | 7/1997 | Hart |
| 5,643,294 A | 7/1997 | Tovey et al. |
| 5,644,798 A | 7/1997 | Shah |
| 5,645,083 A | 7/1997 | Essig et al. |
| 5,645,565 A | 7/1997 | Rudd et al. |

(56) References Cited

U.S. PATENT DOCUMENTS

| | | |
|---|---|---|
| 5,649,372 A | 7/1997 | Souza |
| 5,653,677 A | 8/1997 | Okada et al. |
| 5,653,690 A | 8/1997 | Booth et al. |
| 5,653,722 A | 8/1997 | Kieturakis |
| 5,657,755 A | 8/1997 | Desai |
| 5,662,621 A * | 9/1997 | Lafontaine ............... 604/528 |
| 5,662,663 A | 9/1997 | Shallman |
| 5,667,527 A | 9/1997 | Cook |
| 5,669,875 A | 9/1997 | van Eerdenburg |
| 5,681,324 A | 10/1997 | Kammerer et al. |
| 5,681,330 A | 10/1997 | Hughett et al. |
| 5,685,820 A | 11/1997 | Riek et al. |
| 5,690,606 A | 11/1997 | Slotman |
| 5,690,656 A | 11/1997 | Cope et al. |
| 5,690,660 A | 11/1997 | Kauker et al. |
| 5,695,448 A | 12/1997 | Kimura et al. |
| 5,695,505 A | 12/1997 | Yoon |
| 5,695,511 A | 12/1997 | Cano et al. |
| 5,700,275 A | 12/1997 | Bell et al. |
| 5,702,438 A | 12/1997 | Avitall |
| 5,704,892 A | 1/1998 | Adair |
| 5,709,708 A | 1/1998 | Thal |
| 5,711,921 A | 1/1998 | Langford |
| 5,716,326 A | 2/1998 | Dannan |
| 5,716,375 A | 2/1998 | Fowler |
| 5,728,094 A | 3/1998 | Edwards |
| 5,730,740 A | 3/1998 | Wales et al. |
| 5,735,849 A | 4/1998 | Baden et al. |
| 5,741,234 A | 4/1998 | Aboul-Hosn |
| 5,741,278 A | 4/1998 | Stevens |
| 5,741,285 A | 4/1998 | McBrayer et al. |
| 5,741,429 A | 4/1998 | Donadio, III et al. |
| 5,743,456 A | 4/1998 | Jones et al. |
| 5,746,759 A | 5/1998 | Meade et al. |
| 5,749,826 A | 5/1998 | Faulkner |
| 5,749,881 A | 5/1998 | Sackier et al. |
| 5,749,889 A | 5/1998 | Bacich et al. |
| 5,752,951 A | 5/1998 | Yanik |
| 5,755,731 A | 5/1998 | Grinberg |
| 5,762,604 A | 6/1998 | Kieturakis |
| 5,766,167 A | 6/1998 | Eggers et al. |
| 5,766,170 A | 6/1998 | Eggers |
| 5,766,205 A | 6/1998 | Zvenyatsky et al. |
| 5,769,849 A | 6/1998 | Eggers |
| 5,779,701 A | 7/1998 | McBrayer et al. |
| 5,779,716 A | 7/1998 | Cano et al. |
| 5,779,727 A | 7/1998 | Orejola |
| 5,782,859 A | 7/1998 | Nicholas et al. |
| 5,782,861 A | 7/1998 | Cragg et al. |
| 5,782,866 A | 7/1998 | Wenstrom, Jr. |
| 5,791,022 A | 8/1998 | Bohman |
| 5,792,113 A | 8/1998 | Kramer et al. |
| 5,792,153 A | 8/1998 | Swain et al. |
| 5,792,165 A | 8/1998 | Klieman et al. |
| 5,797,835 A | 8/1998 | Green |
| 5,797,928 A | 8/1998 | Kogasaka |
| 5,797,939 A | 8/1998 | Yoon |
| 5,797,941 A | 8/1998 | Schulze et al. |
| 5,797,959 A | 8/1998 | Castro et al. |
| 5,803,903 A | 9/1998 | Athas et al. |
| 5,808,665 A | 9/1998 | Green |
| 5,810,806 A | 9/1998 | Ritchart et al. |
| 5,810,849 A | 9/1998 | Kontos |
| 5,810,865 A | 9/1998 | Koscher et al. |
| 5,810,876 A | 9/1998 | Kelleher |
| 5,810,877 A | 9/1998 | Roth et al. |
| 5,813,976 A | 9/1998 | Filipi et al. |
| 5,814,058 A | 9/1998 | Carlson et al. |
| 5,817,061 A | 10/1998 | Goodwin et al. |
| 5,817,107 A | 10/1998 | Schaller |
| 5,817,119 A | 10/1998 | Klieman et al. |
| 5,819,736 A | 10/1998 | Avny et al. |
| 5,823,947 A | 10/1998 | Yoon et al. |
| 5,824,071 A | 10/1998 | Nelson et al. |
| 5,827,276 A | 10/1998 | LeVeen et al. |
| 5,827,281 A | 10/1998 | Levin |
| 5,827,299 A | 10/1998 | Thomason et al. |
| 5,827,323 A | 10/1998 | Klieman et al. |
| 5,830,231 A | 11/1998 | Geiges, Jr. |
| 5,833,603 A | 11/1998 | Kovacs et al. |
| 5,833,700 A | 11/1998 | Fogelberg et al. |
| 5,833,703 A | 11/1998 | Manushakian |
| 5,836,960 A | 11/1998 | Kolesa et al. |
| 5,843,017 A | 12/1998 | Yoon |
| 5,843,121 A | 12/1998 | Yoon |
| 5,849,022 A | 12/1998 | Sakashita et al. |
| 5,853,374 A | 12/1998 | Hart et al. |
| 5,855,585 A | 1/1999 | Kontos |
| 5,860,913 A | 1/1999 | Yamaya et al. |
| 5,860,995 A | 1/1999 | Berkelaar |
| 5,868,762 A | 2/1999 | Cragg et al. |
| 5,876,411 A | 3/1999 | Kontos |
| 5,882,331 A | 3/1999 | Sasaki |
| 5,882,344 A | 3/1999 | Stouder, Jr. |
| 5,893,846 A | 4/1999 | Bales et al. |
| 5,893,874 A | 4/1999 | Bourque et al. |
| 5,893,875 A | 4/1999 | O'Connor et al. |
| 5,897,487 A | 4/1999 | Ouchi |
| 5,899,919 A | 5/1999 | Eubanks, Jr. et al. |
| 5,902,238 A | 5/1999 | Golden et al. |
| 5,902,254 A | 5/1999 | Magram |
| 5,904,702 A | 5/1999 | Ek et al. |
| 5,908,420 A | 6/1999 | Parins et al. |
| 5,908,429 A | 6/1999 | Yoon |
| 5,911,737 A | 6/1999 | Lee et al. |
| 5,916,146 A | 6/1999 | Allotta et al. |
| 5,916,147 A | 6/1999 | Boury |
| 5,921,993 A | 7/1999 | Yoon |
| 5,921,997 A | 7/1999 | Fogelberg et al. |
| 5,922,008 A | 7/1999 | Gimpelson |
| 5,925,052 A | 7/1999 | Simmons |
| 5,928,255 A | 7/1999 | Meade et al. |
| 5,928,266 A | 7/1999 | Kontos |
| 5,936,536 A | 8/1999 | Morris |
| 5,944,718 A | 8/1999 | Austin et al. |
| 5,951,547 A | 9/1999 | Gough et al. |
| 5,951,549 A | 9/1999 | Richardson et al. |
| 5,954,720 A | 9/1999 | Wilson et al. |
| 5,954,731 A | 9/1999 | Yoon |
| 5,957,936 A | 9/1999 | Yoon et al. |
| 5,957,943 A | 9/1999 | Vaitekunas |
| 5,957,953 A | 9/1999 | DiPoto et al. |
| 5,964,782 A | 10/1999 | Lafontaine et al. |
| 5,970,581 A | 10/1999 | Chadwick et al. |
| 5,971,995 A | 10/1999 | Rousseau |
| 5,972,002 A | 10/1999 | Bark et al. |
| 5,976,074 A | 11/1999 | Moriyama |
| 5,976,075 A | 11/1999 | Beane et al. |
| 5,976,130 A | 11/1999 | McBrayer et al. |
| 5,976,131 A | 11/1999 | Guglielmi et al. |
| 5,980,539 A | 11/1999 | Kontos |
| 5,980,556 A | 11/1999 | Giordano et al. |
| 5,984,938 A | 11/1999 | Yoon |
| 5,984,939 A | 11/1999 | Yoon |
| 5,984,950 A | 11/1999 | Cragg et al. |
| 5,989,182 A | 11/1999 | Hori et al. |
| 5,993,447 A | 11/1999 | Blewett et al. |
| 5,993,474 A | 11/1999 | Ouchi |
| 5,995,875 A | 11/1999 | Blewett et al. |
| 5,997,555 A | 12/1999 | Kontos |
| 6,001,120 A | 12/1999 | Levin |
| 6,004,269 A | 12/1999 | Crowley et al. |
| 6,004,330 A | 12/1999 | Middleman et al. |
| 6,007,566 A | 12/1999 | Wenstrom, Jr. |
| 6,010,515 A | 1/2000 | Swain et al. |
| 6,012,494 A | 1/2000 | Balazs |
| 6,016,452 A | 1/2000 | Kasevich |
| 6,017,356 A | 1/2000 | Frederick et al. |
| 6,019,770 A | 2/2000 | Christoudias |
| 6,024,708 A | 2/2000 | Bales et al. |
| 6,024,747 A | 2/2000 | Kontos |
| 6,027,522 A | 2/2000 | Palmer |
| 6,030,365 A | 2/2000 | Laufer |
| 6,030,384 A | 2/2000 | Nezhat |

(56) References Cited

U.S. PATENT DOCUMENTS

| | | | |
|---|---|---|---|
| 6,030,634 A | 2/2000 | Wu et al. |
| 6,033,399 A | 3/2000 | Gines |
| 6,036,640 A | 3/2000 | Corace et al. |
| 6,036,685 A | 3/2000 | Mueller |
| 6,053,927 A | 4/2000 | Hamas |
| 6,053,937 A | 4/2000 | Edwards et al. |
| 6,066,160 A | 5/2000 | Colvin et al. |
| 6,068,603 A | 5/2000 | Suzuki |
| 6,068,629 A | 5/2000 | Haissaguerre et al. |
| 6,071,233 A | 6/2000 | Ishikawa et al. |
| 6,074,408 A | 6/2000 | Freeman |
| 6,086,530 A | 7/2000 | Mack |
| 6,090,105 A | 7/2000 | Zepeda et al. |
| 6,090,108 A | 7/2000 | McBrayer et al. |
| 6,090,129 A | 7/2000 | Ouchi |
| 6,096,046 A | 8/2000 | Weiss |
| 6,102,909 A | 8/2000 | Chen et al. |
| 6,102,926 A | 8/2000 | Tartaglia et al. |
| 6,106,473 A | 8/2000 | Violante et al. |
| 6,106,521 A | 8/2000 | Blewett et al. |
| 6,109,852 A | 8/2000 | Shahinpoor et al. |
| 6,110,154 A | 8/2000 | Shimomura et al. |
| 6,110,183 A | 8/2000 | Cope |
| 6,113,593 A | 9/2000 | Tu et al. |
| 6,117,144 A | 9/2000 | Nobles et al. |
| 6,117,158 A | 9/2000 | Measamer et al. |
| 6,139,555 A | 10/2000 | Hart et al. |
| 6,141,037 A | 10/2000 | Upton et al. |
| 6,146,391 A | 11/2000 | Cigaina |
| 6,148,222 A | 11/2000 | Ramsey, III |
| 6,149,653 A | 11/2000 | Deslauriers |
| 6,149,662 A | 11/2000 | Pugliesi et al. |
| 6,152,920 A | 11/2000 | Thompson et al. |
| 6,156,006 A | 12/2000 | Brosens et al. |
| 6,159,200 A | 12/2000 | Verdura et al. |
| 6,165,175 A | 12/2000 | Wampler et al. |
| 6,165,184 A | 12/2000 | Verdura et al. |
| 6,168,570 B1 | 1/2001 | Ferrera |
| 6,168,605 B1 | 1/2001 | Measamer et al. |
| 6,169,269 B1 * | 1/2001 | Maynard ............ 219/209 |
| 6,170,130 B1 | 1/2001 | Hamilton et al. |
| 6,173,872 B1 * | 1/2001 | Cohen ............... 223/96 |
| 6,179,776 B1 | 1/2001 | Adams et al. |
| 6,179,832 B1 | 1/2001 | Jones et al. |
| 6,179,837 B1 | 1/2001 | Hooven |
| 6,183,420 B1 | 2/2001 | Douk et al. |
| 6,190,353 B1 | 2/2001 | Makower et al. |
| 6,190,383 B1 | 2/2001 | Schmaltz et al. |
| 6,190,384 B1 | 2/2001 | Ouchi |
| 6,190,399 B1 | 2/2001 | Palmer et al. |
| 6,203,533 B1 | 3/2001 | Ouchi |
| 6,206,872 B1 | 3/2001 | Lafond et al. |
| 6,206,877 B1 | 3/2001 | Kese et al. |
| 6,206,904 B1 | 3/2001 | Ouchi |
| 6,210,409 B1 | 4/2001 | Ellman et al. |
| 6,214,007 B1 | 4/2001 | Anderson |
| 6,214,028 B1 | 4/2001 | Yoon et al. |
| 6,216,043 B1 | 4/2001 | Swanson et al. |
| 6,228,096 B1 | 5/2001 | Marchand |
| 6,231,506 B1 | 5/2001 | Hu et al. |
| 6,234,958 B1 | 5/2001 | Snoke et al. |
| 6,245,079 B1 | 6/2001 | Nobles et al. |
| 6,246,914 B1 | 6/2001 | de la Rama et al. |
| 6,258,064 B1 | 7/2001 | Smith et al. |
| 6,261,242 B1 | 7/2001 | Roberts et al. |
| 6,264,664 B1 | 7/2001 | Avellanet |
| 6,270,497 B1 | 8/2001 | Sekino et al. |
| 6,270,505 B1 | 8/2001 | Yoshida et al. |
| 6,277,136 B1 | 8/2001 | Bonutti |
| 6,283,963 B1 | 9/2001 | Regula |
| 6,293,909 B1 | 9/2001 | Chu et al. |
| 6,293,952 B1 | 9/2001 | Brosens et al. |
| 6,296,630 B1 | 10/2001 | Altman et al. |
| 6,314,963 B1 | 11/2001 | Vaska et al. |
| 6,322,578 B1 | 11/2001 | Houle et al. |
| 6,325,534 B1 | 12/2001 | Hawley et al. |
| 6,326,177 B1 | 12/2001 | Schoenbach et al. |
| 6,328,730 B1 | 12/2001 | Harkrider, Jr. |
| 6,350,267 B1 | 2/2002 | Stefanchik |
| 6,350,278 B1 | 2/2002 | Lenker et al. |
| 6,352,503 B1 | 3/2002 | Matsui et al. |
| 6,352,543 B1 | 3/2002 | Cole |
| 6,355,013 B1 | 3/2002 | van Muiden |
| 6,355,035 B1 | 3/2002 | Manushakian |
| 6,361,534 B1 | 3/2002 | Chen et al. |
| 6,364,879 B1 | 4/2002 | Chen et al. |
| 6,368,340 B2 | 4/2002 | Malecki et al. |
| 6,371,956 B1 | 4/2002 | Wilson et al. |
| 6,379,366 B1 | 4/2002 | Fleischman et al. |
| 6,383,195 B1 | 5/2002 | Richard |
| 6,383,197 B1 | 5/2002 | Conlon et al. |
| 6,387,671 B1 | 5/2002 | Rubinsky et al. |
| 6,391,029 B1 | 5/2002 | Hooven et al. |
| 6,398,708 B1 | 6/2002 | Hastings et al. |
| 6,402,735 B1 | 6/2002 | Langevin |
| 6,402,746 B1 | 6/2002 | Whayne et al. |
| 6,406,440 B1 | 6/2002 | Stefanchik |
| 6,409,727 B1 | 6/2002 | Bales et al. |
| 6,409,733 B1 | 6/2002 | Conlon et al. |
| 6,419,639 B2 | 7/2002 | Walther et al. |
| 6,419,641 B1 | 7/2002 | Mark et al. |
| 6,427,089 B1 | 7/2002 | Knowlton |
| 6,431,500 B1 | 8/2002 | Jacobs et al. |
| 6,436,107 B1 | 8/2002 | Wang et al. |
| 6,443,970 B1 | 9/2002 | Schulze et al. |
| 6,443,988 B2 | 9/2002 | Felt et al. |
| 6,447,511 B1 | 9/2002 | Slater |
| 6,447,523 B1 | 9/2002 | Middleman et al. |
| 6,454,783 B1 | 9/2002 | Piskun |
| 6,454,785 B2 | 9/2002 | De Hoyos Garza |
| 6,458,076 B1 | 10/2002 | Pruitt |
| 6,464,701 B1 | 10/2002 | Hooven et al. |
| 6,464,702 B2 | 10/2002 | Schulze et al. |
| 6,470,218 B1 | 10/2002 | Behl |
| 6,475,104 B1 | 11/2002 | Lutz et al. |
| 6,485,411 B1 | 11/2002 | Konstorum et al. |
| 6,489,745 B1 | 12/2002 | Koreis |
| 6,491,626 B1 | 12/2002 | Stone et al. |
| 6,491,627 B1 | 12/2002 | Komi |
| 6,491,691 B1 | 12/2002 | Morley et al. |
| 6,493,590 B1 | 12/2002 | Wessman et al. |
| 6,494,893 B2 | 12/2002 | Dubrul et al. |
| 6,500,176 B1 | 12/2002 | Truckai et al. |
| 6,503,192 B1 | 1/2003 | Ouchi |
| 6,506,190 B1 | 1/2003 | Walshe |
| 6,508,827 B1 | 1/2003 | Manhes |
| 6,514,239 B2 | 2/2003 | Shimmura et al. |
| 6,520,954 B2 | 2/2003 | Ouchi |
| 6,526,320 B2 | 2/2003 | Mitchell |
| 6,527,782 B2 | 3/2003 | Hogg et al. |
| 6,530,922 B2 | 3/2003 | Cosman et al. |
| 6,535,764 B2 | 3/2003 | Imran et al. |
| 6,537,200 B2 | 3/2003 | Leysieffer et al. |
| 6,543,456 B1 | 4/2003 | Freeman |
| 6,551,270 B1 | 4/2003 | Bimbo et al. |
| 6,554,766 B2 | 4/2003 | Maeda et al. |
| 6,554,823 B2 | 4/2003 | Palmer et al. |
| 6,554,829 B2 | 4/2003 | Schulze et al. |
| 6,558,384 B2 | 5/2003 | Mayenberger |
| 6,562,034 B2 | 5/2003 | Edwards et al. |
| 6,562,035 B1 | 5/2003 | Levin |
| 6,562,052 B2 | 5/2003 | Nobles et al. |
| 6,569,159 B1 | 5/2003 | Edwards et al. |
| 6,572,629 B2 | 6/2003 | Kalloo et al. |
| 6,572,635 B1 | 6/2003 | Bonutti |
| 6,575,988 B2 | 6/2003 | Rousseau |
| 6,579,311 B1 | 6/2003 | Makower |
| 6,581,889 B2 | 6/2003 | Carpenter et al. |
| 6,585,642 B2 | 7/2003 | Christopher |
| 6,585,717 B1 | 7/2003 | Wittenberger et al. |
| 6,587,750 B2 | 7/2003 | Gerbi et al. |
| 6,592,559 B1 | 7/2003 | Pakter et al. |
| 6,592,603 B2 | 7/2003 | Lasner |
| 6,602,262 B2 | 8/2003 | Griego et al. |

(56) References Cited

U.S. PATENT DOCUMENTS

| | | |
|---|---|---|
| 6,605,105 B1 | 8/2003 | Cuschieri et al. |
| 6,610,072 B1 | 8/2003 | Christy et al. |
| 6,610,074 B2 | 8/2003 | Santilli |
| 6,613,038 B2 | 9/2003 | Bonutti et al. |
| 6,613,068 B2 | 9/2003 | Ouchi |
| 6,616,632 B2 | 9/2003 | Sharp et al. |
| 6,620,193 B1 | 9/2003 | Lau et al. |
| 6,623,448 B2 | 9/2003 | Slater |
| 6,626,919 B1 | 9/2003 | Swanstrom |
| 6,632,229 B1 | 10/2003 | Yamanouchi |
| 6,632,234 B2 | 10/2003 | Kieturakis et al. |
| 6,638,275 B1 | 10/2003 | McGaffigan et al. |
| 6,638,286 B1 | 10/2003 | Burbank et al. |
| 6,645,225 B1 | 11/2003 | Atkinson |
| 6,652,518 B2 | 11/2003 | Wellman et al. |
| 6,652,521 B2 | 11/2003 | Schulze |
| 6,652,551 B1 | 11/2003 | Heiss |
| 6,656,194 B1 | 12/2003 | Gannoe et al. |
| 6,663,641 B1 | 12/2003 | Kovac et al. |
| 6,663,655 B2 | 12/2003 | Ginn et al. |
| 6,666,854 B1 | 12/2003 | Lange |
| 6,672,338 B1 | 1/2004 | Esashi et al. |
| 6,673,058 B2 | 1/2004 | Snow |
| 6,673,087 B1 | 1/2004 | Chang et al. |
| 6,673,092 B1 | 1/2004 | Bacher |
| 6,679,882 B1 | 1/2004 | Kornerup |
| 6,685,628 B2 | 2/2004 | Vu |
| 6,685,724 B1 | 2/2004 | Haluck |
| 6,692,445 B2 | 2/2004 | Roberts et al. |
| 6,692,462 B2 | 2/2004 | Mackenzie et al. |
| 6,692,493 B2 | 2/2004 | McGovern et al. |
| 6,699,180 B2 | 3/2004 | Kobayashi |
| 6,699,256 B1 | 3/2004 | Logan et al. |
| 6,699,263 B2 | 3/2004 | Cope |
| 6,706,018 B2 | 3/2004 | Westlund et al. |
| 6,708,066 B2 | 3/2004 | Herbst et al. |
| 6,709,188 B2 | 3/2004 | Ushimaru |
| 6,709,445 B2 | 3/2004 | Boebel et al. |
| 6,716,226 B2 | 4/2004 | Sixto, Jr. et al. |
| 6,731,875 B1 | 5/2004 | Kartalopoulos |
| 6,736,822 B2 | 5/2004 | McClellan et al. |
| 6,740,030 B2 | 5/2004 | Martone et al. |
| 6,743,166 B2 | 6/2004 | Berci et al. |
| 6,743,226 B2 | 6/2004 | Cosman et al. |
| 6,743,239 B1 | 6/2004 | Kuehn et al. |
| 6,743,240 B2 | 6/2004 | Smith et al. |
| 6,749,560 B1 | 6/2004 | Konstorum et al. |
| 6,749,609 B1 | 6/2004 | Lunsford et al. |
| 6,752,768 B2 | 6/2004 | Burdorff et al. |
| 6,752,811 B2 | 6/2004 | Chu et al. |
| 6,752,822 B2 | 6/2004 | Jespersen |
| 6,758,857 B2 | 7/2004 | Cioanta et al. |
| 6,761,685 B2 | 7/2004 | Adams et al. |
| 6,761,718 B2 | 7/2004 | Madsen |
| 6,761,722 B2 | 7/2004 | Cole et al. |
| 6,773,434 B2 | 8/2004 | Ciarrocca |
| 6,776,787 B2 | 8/2004 | Phung et al. |
| 6,780,151 B2 | 8/2004 | Grabover et al. |
| 6,780,352 B2 | 8/2004 | Jacobson |
| 6,783,491 B2 | 8/2004 | Saadat et al. |
| 6,786,382 B1 | 9/2004 | Hoffman |
| 6,786,864 B2 | 9/2004 | Matsuura et al. |
| 6,786,905 B2 | 9/2004 | Swanson et al. |
| 6,788,977 B2 | 9/2004 | Fenn et al. |
| 6,790,173 B2 | 9/2004 | Saadat et al. |
| 6,790,217 B2 | 9/2004 | Schulze et al. |
| 6,795,728 B2 | 9/2004 | Chornenky et al. |
| 6,800,056 B2 | 10/2004 | Tartaglia et al. |
| 6,808,491 B2 | 10/2004 | Kortenbach et al. |
| 6,817,974 B2 | 11/2004 | Cooper et al. |
| 6,818,007 B1 | 11/2004 | Dampney et al. |
| 6,824,548 B2 | 11/2004 | Smith et al. |
| 6,830,545 B2 | 12/2004 | Bendall |
| 6,836,688 B2 | 12/2004 | Ingle et al. |
| 6,837,847 B2 | 1/2005 | Ewers et al. |
| 6,840,246 B2 | 1/2005 | Downing |
| 6,840,938 B1 | 1/2005 | Morley et al. |
| 6,843,794 B2 | 1/2005 | Sixto, Jr. et al. |
| 6,861,250 B1 | 3/2005 | Cole et al. |
| 6,866,627 B2 | 3/2005 | Nozue |
| 6,866,628 B2 | 3/2005 | Goodman et al. |
| 6,869,394 B2 | 3/2005 | Ishibiki |
| 6,878,106 B1 | 4/2005 | Herrmann |
| 6,878,110 B2 | 4/2005 | Yang et al. |
| 6,881,213 B2 | 4/2005 | Ryan et al. |
| 6,881,216 B2 | 4/2005 | Di Caprio et al. |
| 6,884,213 B2 | 4/2005 | Raz et al. |
| 6,887,255 B2 | 5/2005 | Shimm |
| 6,889,089 B2 | 5/2005 | Behl et al. |
| 6,896,683 B1 | 5/2005 | Gadberry et al. |
| 6,896,692 B2 | 5/2005 | Ginn et al. |
| 6,899,710 B2 | 5/2005 | Hooven |
| 6,908,427 B2 | 6/2005 | Fleener et al. |
| 6,908,476 B2 | 6/2005 | Jud et al. |
| 6,913,613 B2 | 7/2005 | Schwarz et al. |
| 6,916,284 B2 | 7/2005 | Moriyama |
| 6,918,871 B2 | 7/2005 | Schulze |
| 6,918,908 B2 | 7/2005 | Bonner et al. |
| 6,926,725 B2 | 8/2005 | Cooke et al. |
| 6,932,810 B2 | 8/2005 | Ryan |
| 6,932,824 B1 | 8/2005 | Roop et al. |
| 6,932,827 B2 | 8/2005 | Cole |
| 6,932,834 B2 | 8/2005 | Lizardi et al. |
| 6,936,003 B2 | 8/2005 | Iddan |
| 6,939,327 B2 | 9/2005 | Hall et al. |
| 6,942,613 B2 | 9/2005 | Ewers et al. |
| 6,944,490 B1 | 9/2005 | Chow |
| 6,945,472 B2 | 9/2005 | Wuttke et al. |
| 6,945,979 B2 | 9/2005 | Kortenbach et al. |
| 6,955,683 B2 | 10/2005 | Bonutti |
| 6,958,035 B2 | 10/2005 | Friedman et al. |
| 6,960,162 B2 | 11/2005 | Saadat et al. |
| 6,960,163 B2 | 11/2005 | Ewers et al. |
| 6,962,587 B2 | 11/2005 | Johnson et al. |
| 6,964,662 B2 | 11/2005 | Kidooka |
| 6,966,909 B2 | 11/2005 | Marshall et al. |
| 6,966,919 B2 | 11/2005 | Sixto, Jr. et al. |
| 6,967,462 B1 | 11/2005 | Landis |
| 6,971,988 B2 | 12/2005 | Orban, III |
| 6,972,017 B2 | 12/2005 | Smith et al. |
| 6,974,411 B2 | 12/2005 | Belson |
| 6,976,992 B2 | 12/2005 | Sachatello et al. |
| 6,984,203 B2 | 1/2006 | Tartaglia et al. |
| 6,984,205 B2 | 1/2006 | Gazdzinski |
| 6,986,774 B2 | 1/2006 | Middleman et al. |
| 6,988,987 B2 | 1/2006 | Ishikawa et al. |
| 6,989,028 B2 | 1/2006 | Lashinski et al. |
| 6,991,627 B2 | 1/2006 | Madhani et al. |
| 6,991,631 B2 | 1/2006 | Woloszko et al. |
| 6,994,708 B2 | 2/2006 | Manzo |
| 6,997,870 B2 * | 2/2006 | Couvillon, Jr. ............... 600/146 |
| 6,997,931 B2 | 2/2006 | Sauer et al. |
| 7,000,818 B2 | 2/2006 | Shelton, IV et al. |
| 7,001,341 B2 | 2/2006 | Gellman et al. |
| 7,008,375 B2 | 3/2006 | Weisel |
| 7,008,419 B2 | 3/2006 | Shadduck |
| 7,009,634 B2 | 3/2006 | Iddan et al. |
| 7,010,340 B2 | 3/2006 | Scarantino et al. |
| 7,020,531 B1 | 3/2006 | Colliou et al. |
| 7,025,580 B2 | 4/2006 | Heagy et al. |
| 7,029,435 B2 | 4/2006 | Nakao |
| 7,029,438 B2 | 4/2006 | Morin et al. |
| 7,029,450 B2 | 4/2006 | Gellman |
| 7,032,600 B2 | 4/2006 | Fukuda et al. |
| 7,035,680 B2 | 4/2006 | Partridge et al. |
| 7,037,290 B2 | 5/2006 | Gardeski et al. |
| 7,041,052 B2 | 5/2006 | Saadat et al. |
| 7,052,489 B2 | 5/2006 | Griego et al. |
| 7,060,024 B2 | 6/2006 | Long et al. |
| 7,060,025 B2 | 6/2006 | Long et al. |
| 7,063,697 B2 | 6/2006 | Slater |
| 7,063,715 B2 | 6/2006 | Onuki et al. |
| 7,066,879 B2 | 6/2006 | Fowler et al. |
| 7,066,936 B2 | 6/2006 | Ryan |

(56) References Cited

U.S. PATENT DOCUMENTS

| | | |
|---|---|---|
| 7,070,602 B2 | 7/2006 | Smith et al. |
| 7,076,305 B2 | 7/2006 | Imran et al. |
| 7,083,618 B2 | 8/2006 | Couture et al. |
| 7,083,620 B2 | 8/2006 | Jahns et al. |
| 7,083,629 B2 | 8/2006 | Weller et al. |
| 7,083,635 B2 | 8/2006 | Ginn |
| 7,087,071 B2 | 8/2006 | Nicholas et al. |
| 7,088,923 B2 | 8/2006 | Haruyama |
| 7,090,673 B2 | 8/2006 | Dycus et al. |
| 7,090,683 B2 | 8/2006 | Brock et al. |
| 7,090,685 B2 | 8/2006 | Kortenbach et al. |
| 7,093,518 B2 | 8/2006 | Gmeilbauer |
| 7,101,371 B2 | 9/2006 | Dycus et al. |
| 7,101,372 B2 | 9/2006 | Dycus et al. |
| 7,101,373 B2 | 9/2006 | Dycus et al. |
| 7,105,000 B2 | 9/2006 | McBrayer |
| 7,105,005 B2 | 9/2006 | Blake |
| 7,108,696 B2 | 9/2006 | Daniel et al. |
| 7,108,703 B2 | 9/2006 | Danitz et al. |
| 7,112,208 B2 | 9/2006 | Morris et al. |
| 7,115,092 B2 | 10/2006 | Park et al. |
| 7,115,124 B1 | 10/2006 | Xiao |
| 7,117,703 B2 | 10/2006 | Kato et al. |
| 7,118,531 B2 | 10/2006 | Krill |
| 7,118,578 B2 | 10/2006 | West, Jr. et al. |
| 7,118,587 B2 | 10/2006 | Dycus et al. |
| 7,128,708 B2 | 10/2006 | Saadat et al. |
| 7,130,697 B2 | 10/2006 | Chornenky et al. |
| RE39,415 E | 11/2006 | Bales et al. |
| 7,131,978 B2 | 11/2006 | Sancoff et al. |
| 7,131,979 B2 | 11/2006 | DiCarlo et al. |
| 7,131,980 B1 | 11/2006 | Field et al. |
| 7,137,980 B2 | 11/2006 | Buysse et al. |
| 7,137,981 B2 | 11/2006 | Long |
| 7,146,984 B2 | 12/2006 | Stack et al. |
| 7,147,650 B2 | 12/2006 | Lee |
| 7,150,097 B2 | 12/2006 | Sremcich et al. |
| 7,150,655 B2 | 12/2006 | Mastrototaro et al. |
| 7,150,750 B2 | 12/2006 | Damarati |
| 7,152,488 B2 | 12/2006 | Hedrich et al. |
| 7,153,321 B2 | 12/2006 | Andrews |
| 7,160,296 B2 | 1/2007 | Pearson et al. |
| 7,163,525 B2 | 1/2007 | Franer |
| 7,172,714 B2 | 2/2007 | Jacobson |
| 7,179,254 B2 | 2/2007 | Pendekanti et al. |
| 7,188,627 B2 | 3/2007 | Nelson et al. |
| 7,195,612 B2 | 3/2007 | Van Sloten et al. |
| 7,195,631 B2 | 3/2007 | Dumbauld |
| 7,204,820 B2 | 4/2007 | Akahoshi |
| 7,208,005 B2 | 4/2007 | Frecker et al. |
| 7,211,092 B2 | 5/2007 | Hughett |
| 7,220,227 B2 | 5/2007 | Sasaki et al. |
| 7,223,272 B2 | 5/2007 | Francere et al. |
| 7,229,438 B2 | 6/2007 | Young |
| 7,232,414 B2 | 6/2007 | Gonzalez |
| 7,232,445 B2 | 6/2007 | Kortenbach et al. |
| 7,235,089 B1 | 6/2007 | McGuckin, Jr. |
| 7,241,290 B2 | 7/2007 | Doyle et al. |
| 7,244,228 B2 | 7/2007 | Lubowski |
| 7,250,027 B2 | 7/2007 | Barry |
| 7,252,660 B2 | 8/2007 | Kunz |
| 7,255,675 B2 | 8/2007 | Gertner et al. |
| 7,261,725 B2 | 8/2007 | Binmoeller |
| 7,270,663 B2 | 9/2007 | Nakao |
| 7,288,075 B2 | 10/2007 | Parihar et al. |
| 7,291,127 B2 * | 11/2007 | Eidenschink ............. 604/95.05 |
| 7,294,139 B1 | 11/2007 | Gengler |
| 7,301,250 B2 | 11/2007 | Cassel |
| 7,306,597 B2 | 12/2007 | Manzo |
| 7,308,828 B2 | 12/2007 | Hashimoto |
| 7,318,802 B2 | 1/2008 | Suzuki et al. |
| 7,320,695 B2 | 1/2008 | Carroll |
| 7,322,934 B2 | 1/2008 | Miyake et al. |
| 7,323,006 B2 | 1/2008 | Andreas et al. |
| 7,329,256 B2 | 2/2008 | Johnson et al. |
| 7,329,257 B2 | 2/2008 | Kanehira et al. |
| 7,329,383 B2 | 2/2008 | Stinson |
| 7,335,220 B2 | 2/2008 | Khosravi et al. |
| 7,344,536 B1 | 3/2008 | Lunsford et al. |
| 7,352,387 B2 | 4/2008 | Yamamoto |
| 7,364,582 B2 | 4/2008 | Lee |
| 7,371,215 B2 | 5/2008 | Colliou et al. |
| 7,381,216 B2 | 6/2008 | Buzzard et al. |
| 7,390,324 B2 | 6/2008 | Whalen et al. |
| 7,393,222 B2 | 7/2008 | Wenchell |
| 7,402,162 B2 | 7/2008 | Ouchi |
| 7,404,791 B2 | 7/2008 | Linares et al. |
| 7,410,483 B2 | 8/2008 | Danitz et al. |
| 7,413,563 B2 | 8/2008 | Corcoran et al. |
| 7,416,554 B2 | 8/2008 | Lam et al. |
| 7,422,590 B2 | 9/2008 | Kupferschmid et al. |
| 7,435,229 B2 | 10/2008 | Wolf |
| 7,435,257 B2 | 10/2008 | Lashinski et al. |
| 7,452,327 B2 | 11/2008 | Durgin et al. |
| 7,455,208 B2 | 11/2008 | Wales et al. |
| 7,468,066 B2 | 12/2008 | Vargas et al. |
| 7,476,237 B2 | 1/2009 | Taniguchi et al. |
| 7,485,093 B2 | 2/2009 | Glukhovsky |
| 7,488,295 B2 | 2/2009 | Burbank et al. |
| 7,494,499 B2 | 2/2009 | Nagase et al. |
| 7,497,867 B2 | 3/2009 | Lasner et al. |
| 7,498,950 B1 | 3/2009 | Ertas et al. |
| 7,507,200 B2 | 3/2009 | Okada |
| 7,510,107 B2 | 3/2009 | Timm et al. |
| 7,511,733 B2 | 3/2009 | Takizawa et al. |
| 7,515,953 B2 | 4/2009 | Madar et al. |
| 7,520,876 B2 | 4/2009 | Ressemann et al. |
| 7,524,281 B2 | 4/2009 | Chu et al. |
| 7,524,302 B2 | 4/2009 | Tower |
| 7,534,228 B2 | 5/2009 | Williams |
| 7,540,872 B2 | 6/2009 | Schechter et al. |
| 7,542,807 B2 | 6/2009 | Bertolero et al. |
| 7,544,203 B2 | 6/2009 | Chin et al. |
| 7,548,040 B2 | 6/2009 | Lee et al. |
| 7,549,564 B2 | 6/2009 | Boudreaux |
| 7,549,998 B2 | 6/2009 | Braun |
| 7,553,278 B2 | 6/2009 | Kucklick |
| 7,553,298 B2 | 6/2009 | Hunt et al. |
| 7,559,452 B2 * | 7/2009 | Wales et al. ............... 227/176.1 |
| 7,559,887 B2 | 7/2009 | Dannan |
| 7,559,916 B2 | 7/2009 | Smith et al. |
| 7,560,006 B2 | 7/2009 | Rakos et al. |
| 7,561,907 B2 | 7/2009 | Fuimaono et al. |
| 7,561,916 B2 | 7/2009 | Hunt et al. |
| 7,566,334 B2 | 7/2009 | Christian et al. |
| 7,575,144 B2 | 8/2009 | Ortiz et al. |
| 7,575,548 B2 | 8/2009 | Takemoto et al. |
| 7,579,550 B2 | 8/2009 | Dayton et al. |
| 7,582,096 B2 | 9/2009 | Gellman et al. |
| 7,588,177 B2 | 9/2009 | Racenet |
| 7,588,557 B2 | 9/2009 | Nakao |
| 7,597,229 B2 | 10/2009 | Boudreaux et al. |
| 7,604,150 B2 | 10/2009 | Boudreaux |
| 7,608,083 B2 | 10/2009 | Lee et al. |
| 7,611,479 B2 | 11/2009 | Cragg et al. |
| 7,618,398 B2 | 11/2009 | Holman et al. |
| 7,621,936 B2 | 11/2009 | Cragg et al. |
| 7,632,250 B2 | 12/2009 | Smith et al. |
| 7,635,373 B2 | 12/2009 | Ortiz |
| 7,637,903 B2 | 12/2009 | Lentz et al. |
| 7,648,519 B2 | 1/2010 | Lee et al. |
| 7,650,742 B2 | 1/2010 | Ushijima |
| 7,651,483 B2 | 1/2010 | Byrum et al. |
| 7,651,509 B2 | 1/2010 | Bojarski et al. |
| 7,654,431 B2 | 2/2010 | Hueil et al. |
| 7,655,004 B2 | 2/2010 | Long |
| 7,662,089 B2 | 2/2010 | Okada et al. |
| 7,666,180 B2 | 2/2010 | Holsten et al. |
| 7,666,203 B2 | 2/2010 | Chanduszko et al. |
| 7,670,336 B2 | 3/2010 | Young et al. |
| 7,674,259 B2 | 3/2010 | Shadduck |
| 7,678,043 B2 | 3/2010 | Gilad |
| 7,680,543 B2 | 3/2010 | Azure |
| 7,684,599 B2 | 3/2010 | Horn et al. |

(56) References Cited

U.S. PATENT DOCUMENTS

| | | |
|---|---|---|
| 7,686,826 B2 | 3/2010 | Lee et al. |
| 7,697,970 B2 | 4/2010 | Uchiyama et al. |
| 7,699,835 B2 | 4/2010 | Lee et al. |
| 7,699,864 B2 | 4/2010 | Kick et al. |
| 7,713,189 B2 | 5/2010 | Hanke |
| 7,713,270 B2 | 5/2010 | Suzuki |
| 7,736,374 B2 | 6/2010 | Vaughan et al. |
| 7,744,615 B2 | 6/2010 | Couture |
| 7,749,161 B2 | 7/2010 | Beckman et al. |
| 7,753,933 B2 | 7/2010 | Ginn et al. |
| 7,758,577 B2 | 7/2010 | Nobis et al. |
| 7,762,949 B2 | 7/2010 | Nakao |
| 7,762,998 B2 | 7/2010 | Birk et al. |
| 7,763,012 B2 | 7/2010 | Petrick et al. |
| 7,765,010 B2 | 7/2010 | Chornenky et al. |
| 7,771,416 B2 | 8/2010 | Spivey et al. |
| 7,771,437 B2 | 8/2010 | Hogg et al. |
| 7,780,683 B2 | 8/2010 | Roue et al. |
| 7,780,691 B2 | 8/2010 | Stefanchik |
| 7,784,663 B2 | 8/2010 | Shelton, IV |
| 7,794,409 B2 | 9/2010 | Damarati |
| 7,794,475 B2 | 9/2010 | Hess et al. |
| 7,798,386 B2 | 9/2010 | Schall et al. |
| 7,815,662 B2 | 10/2010 | Spivey et al. |
| 7,828,186 B2 | 11/2010 | Wales |
| 7,833,156 B2 | 11/2010 | Williams et al. |
| 7,837,615 B2 | 11/2010 | Le et al. |
| 7,842,028 B2 | 11/2010 | Lee |
| 7,842,068 B2 | 11/2010 | Ginn |
| 7,846,171 B2 | 12/2010 | Kullas et al. |
| 7,850,660 B2 | 12/2010 | Uth et al. |
| 7,857,183 B2 | 12/2010 | Shelton, IV |
| 7,862,546 B2 | 1/2011 | Conlon et al. |
| 7,867,216 B2 | 1/2011 | Wahr et al. |
| 7,892,220 B2 | 2/2011 | Faller et al. |
| 7,896,804 B2 | 3/2011 | Uchimura et al. |
| 7,896,887 B2 | 3/2011 | Rimbaugh et al. |
| 7,905,828 B2 | 3/2011 | Brock et al. |
| 7,909,809 B2 | 3/2011 | Scopton et al. |
| 7,914,513 B2 | 3/2011 | Voorhees, Jr. |
| 7,918,869 B2 | 4/2011 | Saadat et al. |
| 7,927,271 B2 | 4/2011 | Dimitriou et al. |
| 7,931,624 B2 | 4/2011 | Smith et al. |
| 7,945,332 B2 | 5/2011 | Schechter |
| 7,947,000 B2 | 5/2011 | Vargas et al. |
| 7,953,326 B2 | 5/2011 | Farr et al. |
| 7,955,298 B2 | 6/2011 | Carroll et al. |
| 7,963,975 B2 | 6/2011 | Criscuolo |
| 7,965,180 B2 | 6/2011 | Koyama |
| 7,967,808 B2 | 6/2011 | Fitzgerald et al. |
| 7,969,473 B2 | 6/2011 | Kotoda |
| 7,972,330 B2 | 7/2011 | Alejandro et al. |
| 7,976,552 B2 | 7/2011 | Suzuki |
| 7,985,239 B2 | 7/2011 | Suzuki |
| 7,988,685 B2 | 8/2011 | Ziaie et al. |
| 8,029,504 B2 | 10/2011 | Long |
| 8,037,591 B2 | 10/2011 | Spivey et al. |
| 8,048,067 B2 | 11/2011 | Davalos et al. |
| 8,057,510 B2 | 11/2011 | Ginn et al. |
| 8,062,311 B2 | 11/2011 | Litscher et al. |
| 8,066,632 B2 | 11/2011 | Dario et al. |
| 8,075,587 B2 | 12/2011 | Ginn |
| 8,088,062 B2 | 1/2012 | Zwolinski |
| 8,096,459 B2 | 1/2012 | Ortiz et al. |
| 8,118,821 B2 | 2/2012 | Mouw |
| 8,147,424 B2 | 4/2012 | Kassab et al. |
| 8,157,813 B2 | 4/2012 | Ko et al. |
| 8,182,414 B2 | 5/2012 | Handa et al. |
| 8,206,295 B2 | 6/2012 | Kaul |
| 8,221,310 B2 | 7/2012 | Saadat et al. |
| 8,303,581 B2 | 11/2012 | Arts et al. |
| 8,430,811 B2 | 4/2013 | Hess et al. |
| 2001/0023333 A1 | 9/2001 | Wise et al. |
| 2001/0049497 A1 | 12/2001 | Kalloo et al. |
| 2002/0022771 A1 | 2/2002 | Diokno et al. |
| 2002/0022857 A1 | 2/2002 | Goldsteen et al. |
| 2002/0023353 A1 | 2/2002 | Ting-Kung |
| 2002/0029055 A1 | 3/2002 | Bonutti |
| 2002/0042562 A1 | 4/2002 | Meron et al. |
| 2002/0049439 A1 | 4/2002 | Mulier et al. |
| 2002/0068945 A1 | 6/2002 | Sixto, Jr. et al. |
| 2002/0078967 A1 | 6/2002 | Sixto, Jr. et al. |
| 2002/0082516 A1 | 6/2002 | Stefanchik |
| 2002/0095164 A1 | 7/2002 | Andreas et al. |
| 2002/0107530 A1 | 8/2002 | Sauer et al. |
| 2002/0133115 A1 | 9/2002 | Gordon et al. |
| 2002/0138086 A1 | 9/2002 | Sixto, Jr. et al. |
| 2002/0147456 A1 | 10/2002 | Diduch et al. |
| 2002/0165592 A1 | 11/2002 | Glukhovsky et al. |
| 2002/0173805 A1 | 11/2002 | Matsuno et al. |
| 2002/0183591 A1 | 12/2002 | Matsuura et al. |
| 2003/0014090 A1 | 1/2003 | Abrahamson |
| 2003/0023255 A1 | 1/2003 | Miles et al. |
| 2003/0036679 A1 | 2/2003 | Kortenbach et al. |
| 2003/0069602 A1 | 4/2003 | Jacobs et al. |
| 2003/0078471 A1 | 4/2003 | Foley et al. |
| 2003/0083681 A1 | 5/2003 | Moutafis et al. |
| 2003/0114731 A1 | 6/2003 | Cadeddu et al. |
| 2003/0114732 A1 | 6/2003 | Webler et al. |
| 2003/0120257 A1 | 6/2003 | Houston et al. |
| 2003/0124009 A1 | 7/2003 | Ravi et al. |
| 2003/0130564 A1 | 7/2003 | Martone et al. |
| 2003/0130656 A1 | 7/2003 | Levin |
| 2003/0139646 A1 | 7/2003 | Sharrow et al. |
| 2003/0158521 A1 | 8/2003 | Ameri |
| 2003/0167062 A1 | 9/2003 | Gambale et al. |
| 2003/0171651 A1 | 9/2003 | Page et al. |
| 2003/0176880 A1 | 9/2003 | Long et al. |
| 2003/0216611 A1 | 11/2003 | Vu |
| 2003/0216615 A1 | 11/2003 | Ouchi |
| 2003/0220545 A1 | 11/2003 | Ouchi |
| 2003/0225312 A1 | 12/2003 | Suzuki et al. |
| 2003/0225332 A1 | 12/2003 | Okada et al. |
| 2003/0229269 A1 | 12/2003 | Humphrey |
| 2003/0229371 A1 | 12/2003 | Whitworth |
| 2003/0236549 A1 | 12/2003 | Bonadio et al. |
| 2004/0002683 A1 | 1/2004 | Nicholson et al. |
| 2004/0024414 A1 | 2/2004 | Downing |
| 2004/0034369 A1 | 2/2004 | Sauer et al. |
| 2004/0054322 A1 | 3/2004 | Vargas |
| 2004/0098007 A1 | 5/2004 | Heiss |
| 2004/0101456 A1 | 5/2004 | Kuroshima et al. |
| 2004/0104999 A1 | 6/2004 | Okada |
| 2004/0116948 A1 | 6/2004 | Sixto, Jr. et al. |
| 2004/0127940 A1 | 7/2004 | Ginn et al. |
| 2004/0133077 A1 | 7/2004 | Obenchain et al. |
| 2004/0133089 A1 | 7/2004 | Kilcoyne et al. |
| 2004/0136779 A1 | 7/2004 | Bhaskar |
| 2004/0138525 A1 | 7/2004 | Saadat et al. |
| 2004/0138529 A1 | 7/2004 | Wiltshire et al. |
| 2004/0138587 A1 | 7/2004 | Lyons, IV |
| 2004/0161451 A1 | 8/2004 | Pierce et al. |
| 2004/0167545 A1 | 8/2004 | Sadler et al. |
| 2004/0176699 A1 | 9/2004 | Walker et al. |
| 2004/0186350 A1 | 9/2004 | Brenneman et al. |
| 2004/0193009 A1 | 9/2004 | Jaffe et al. |
| 2004/0193146 A1 | 9/2004 | Lee et al. |
| 2004/0193186 A1 | 9/2004 | Kortenbach et al. |
| 2004/0193188 A1 | 9/2004 | Francese |
| 2004/0193189 A1 | 9/2004 | Kortenbach et al. |
| 2004/0193200 A1 | 9/2004 | Dworschak et al. |
| 2004/0199052 A1 | 10/2004 | Banik et al. |
| 2004/0199159 A1 | 10/2004 | Lee et al. |
| 2004/0206859 A1 | 10/2004 | Chong et al. |
| 2004/0210245 A1 | 10/2004 | Erickson et al. |
| 2004/0215058 A1 | 10/2004 | Zirps et al. |
| 2004/0225183 A1 | 11/2004 | Michlitsch et al. |
| 2004/0225186 A1 | 11/2004 | Horne, Jr. et al. |
| 2004/0225323 A1 | 11/2004 | Nagase et al. |
| 2004/0230095 A1 | 11/2004 | Stefanchik et al. |
| 2004/0230096 A1 | 11/2004 | Stefanchik et al. |
| 2004/0230097 A1 | 11/2004 | Stefanchik et al. |
| 2004/0230161 A1 | 11/2004 | Zeiner |
| 2004/0243108 A1 | 12/2004 | Suzuki |

(56) References Cited

U.S. PATENT DOCUMENTS

| | | |
|---|---|---|
| 2004/0249246 A1 | 12/2004 | Campos |
| 2004/0249367 A1 | 12/2004 | Saadat et al. |
| 2004/0249394 A1 | 12/2004 | Morris et al. |
| 2004/0249443 A1 | 12/2004 | Shanley et al. |
| 2004/0254572 A1 | 12/2004 | McIntyre et al. |
| 2004/0260198 A1 | 12/2004 | Rothberg et al. |
| 2004/0260337 A1 | 12/2004 | Freed |
| 2005/0004515 A1 | 1/2005 | Hart et al. |
| 2005/0033265 A1 | 2/2005 | Engel et al. |
| 2005/0033277 A1 | 2/2005 | Clague et al. |
| 2005/0033319 A1 | 2/2005 | Gambale et al. |
| 2005/0033333 A1 | 2/2005 | Smith et al. |
| 2005/0043690 A1 | 2/2005 | Todd |
| 2005/0049616 A1 | 3/2005 | Rivera et al. |
| 2005/0059963 A1 | 3/2005 | Phan et al. |
| 2005/0059964 A1 | 3/2005 | Fitz |
| 2005/0065397 A1 | 3/2005 | Saadat et al. |
| 2005/0065509 A1 | 3/2005 | Coldwell et al. |
| 2005/0065517 A1 | 3/2005 | Chin |
| 2005/0070754 A1 | 3/2005 | Nobis et al. |
| 2005/0070763 A1 | 3/2005 | Nobis et al. |
| 2005/0070764 A1 | 3/2005 | Nobis et al. |
| 2005/0080413 A1 | 4/2005 | Canady |
| 2005/0085693 A1 | 4/2005 | Belson et al. |
| 2005/0085832 A1 | 4/2005 | Sancoff et al. |
| 2005/0090837 A1 | 4/2005 | Sixto, Jr. et al. |
| 2005/0090838 A1 | 4/2005 | Sixto, Jr. et al. |
| 2005/0096502 A1 | 5/2005 | Khalili |
| 2005/0101837 A1 | 5/2005 | Kalloo et al. |
| 2005/0101838 A1 | 5/2005 | Camillocci et al. |
| 2005/0101984 A1 | 5/2005 | Chanduszko et al. |
| 2005/0107663 A1 | 5/2005 | Saadat et al. |
| 2005/0107664 A1 | 5/2005 | Kalloo et al. |
| 2005/0110881 A1 | 5/2005 | Glukhovsky et al. |
| 2005/0113847 A1 | 5/2005 | Gadberry et al. |
| 2005/0119613 A1 | 6/2005 | Moenning et al. |
| 2005/0124855 A1 | 6/2005 | Jaffe et al. |
| 2005/0125010 A1 | 6/2005 | Smith et al. |
| 2005/0131279 A1 | 6/2005 | Boulais et al. |
| 2005/0131457 A1 | 6/2005 | Douglas et al. |
| 2005/0137454 A1 | 6/2005 | Saadat et al. |
| 2005/0143647 A1 | 6/2005 | Minai et al. |
| 2005/0143690 A1 | 6/2005 | High |
| 2005/0143774 A1 | 6/2005 | Polo |
| 2005/0143803 A1 | 6/2005 | Watson et al. |
| 2005/0149087 A1 | 7/2005 | Ahlberg et al. |
| 2005/0149096 A1 | 7/2005 | Hilal et al. |
| 2005/0159648 A1 | 7/2005 | Freed |
| 2005/0165272 A1 | 7/2005 | Okada et al. |
| 2005/0165378 A1 | 7/2005 | Heinrich et al. |
| 2005/0165411 A1 | 7/2005 | Orban, III |
| 2005/0165429 A1 | 7/2005 | Douglas et al. |
| 2005/0182429 A1 | 8/2005 | Yamanouchi |
| 2005/0192478 A1 | 9/2005 | Williams et al. |
| 2005/0192598 A1 | 9/2005 | Johnson et al. |
| 2005/0192602 A1 | 9/2005 | Manzo |
| 2005/0192654 A1 | 9/2005 | Chanduszko et al. |
| 2005/0209624 A1 | 9/2005 | Vijay |
| 2005/0215858 A1 | 9/2005 | Vail, III |
| 2005/0216050 A1 | 9/2005 | Sepetka et al. |
| 2005/0228224 A1 | 10/2005 | Okada et al. |
| 2005/0228406 A1 | 10/2005 | Bose |
| 2005/0234297 A1 | 10/2005 | Devierre et al. |
| 2005/0250983 A1 | 11/2005 | Tremaglio et al. |
| 2005/0250990 A1 | 11/2005 | Le et al. |
| 2005/0250993 A1 | 11/2005 | Jaeger |
| 2005/0251166 A1 | 11/2005 | Vaughan et al. |
| 2005/0251176 A1 | 11/2005 | Swanstrom et al. |
| 2005/0261674 A1 | 11/2005 | Nobis et al. |
| 2005/0267492 A1 | 12/2005 | Poncet et al. |
| 2005/0272975 A1 | 12/2005 | McWeeney et al. |
| 2005/0272977 A1 | 12/2005 | Saadat et al. |
| 2005/0273084 A1 | 12/2005 | Hinman et al. |
| 2005/0274935 A1 | 12/2005 | Nelson |
| 2005/0277945 A1 | 12/2005 | Saadat et al. |
| 2005/0277951 A1 | 12/2005 | Smith et al. |
| 2005/0277952 A1 | 12/2005 | Arp et al. |
| 2005/0277954 A1 | 12/2005 | Smith et al. |
| 2005/0277955 A1 | 12/2005 | Palmer et al. |
| 2005/0277956 A1 | 12/2005 | Francese et al. |
| 2005/0277957 A1 | 12/2005 | Kuhns et al. |
| 2005/0283118 A1 | 12/2005 | Uth et al. |
| 2005/0283119 A1 | 12/2005 | Uth et al. |
| 2005/0288555 A1 | 12/2005 | Binmoeller |
| 2006/0004406 A1 | 1/2006 | Wehrstein et al. |
| 2006/0004409 A1 | 1/2006 | Nobis et al. |
| 2006/0004410 A1 | 1/2006 | Nobis et al. |
| 2006/0015009 A1 | 1/2006 | Jaffe et al. |
| 2006/0015131 A1 | 1/2006 | Kierce et al. |
| 2006/0020167 A1 | 1/2006 | Sitzmann |
| 2006/0020247 A1 | 1/2006 | Kagan et al. |
| 2006/0025654 A1 | 2/2006 | Suzuki et al. |
| 2006/0025781 A1 | 2/2006 | Young et al. |
| 2006/0025812 A1 | 2/2006 | Shelton, IV |
| 2006/0025819 A1 | 2/2006 | Nobis et al. |
| 2006/0036267 A1 | 2/2006 | Saadat et al. |
| 2006/0041188 A1 | 2/2006 | Dirusso et al. |
| 2006/0058582 A1 | 3/2006 | Maahs et al. |
| 2006/0058776 A1 | 3/2006 | Bilsbury |
| 2006/0064083 A1 | 3/2006 | Khalaj et al. |
| 2006/0069396 A1 | 3/2006 | Meade et al. |
| 2006/0069424 A1 | 3/2006 | Acosta et al. |
| 2006/0069425 A1 | 3/2006 | Hillis et al. |
| 2006/0069429 A1 | 3/2006 | Spence et al. |
| 2006/0074413 A1 | 4/2006 | Behzadian |
| 2006/0079890 A1 | 4/2006 | Guerra |
| 2006/0089528 A1 | 4/2006 | Tartaglia et al. |
| 2006/0095031 A1 | 5/2006 | Ormsby |
| 2006/0095060 A1 | 5/2006 | Mayenberger et al. |
| 2006/0100687 A1 | 5/2006 | Fahey et al. |
| 2006/0106423 A1 | 5/2006 | Weisel et al. |
| 2006/0111209 A1 | 5/2006 | Hinman et al. |
| 2006/0111210 A1 | 5/2006 | Hinman et al. |
| 2006/0111704 A1 | 5/2006 | Brenneman et al. |
| 2006/0129166 A1 | 6/2006 | Lavelle |
| 2006/0135962 A1 | 6/2006 | Kick et al. |
| 2006/0135971 A1 | 6/2006 | Swanstrom et al. |
| 2006/0135984 A1 | 6/2006 | Kramer et al. |
| 2006/0142644 A1 | 6/2006 | Mulac et al. |
| 2006/0142652 A1 | 6/2006 | Keenan |
| 2006/0142790 A1 | 6/2006 | Gertner |
| 2006/0142798 A1 | 6/2006 | Holman et al. |
| 2006/0149131 A1 | 7/2006 | Or |
| 2006/0149132 A1 | 7/2006 | Iddan |
| 2006/0149135 A1 | 7/2006 | Paz |
| 2006/0161190 A1 | 7/2006 | Gadberry et al. |
| 2006/0167416 A1 | 7/2006 | Mathis et al. |
| 2006/0167482 A1 | 7/2006 | Swain et al. |
| 2006/0178560 A1 | 8/2006 | Saadat et al. |
| 2006/0183975 A1 | 8/2006 | Saadat et al. |
| 2006/0184161 A1 | 8/2006 | Maahs et al. |
| 2006/0189844 A1 | 8/2006 | Tien |
| 2006/0189845 A1 | 8/2006 | Maahs et al. |
| 2006/0190027 A1 | 8/2006 | Downey |
| 2006/0195084 A1 | 8/2006 | Slater |
| 2006/0200005 A1 | 9/2006 | Bjork et al. |
| 2006/0200121 A1 | 9/2006 | Mowery |
| 2006/0200169 A1 | 9/2006 | Sniffin |
| 2006/0200170 A1 | 9/2006 | Aranyi |
| 2006/0200199 A1 | 9/2006 | Bonutti et al. |
| 2006/0217665 A1 | 9/2006 | Prosek |
| 2006/0217697 A1 | 9/2006 | Lau et al. |
| 2006/0217742 A1 | 9/2006 | Messerly et al. |
| 2006/0217743 A1 | 9/2006 | Messerly et al. |
| 2006/0229639 A1 | 10/2006 | Whitfield |
| 2006/0229640 A1 | 10/2006 | Whitfield |
| 2006/0237022 A1 | 10/2006 | Chen et al. |
| 2006/0237023 A1 | 10/2006 | Cox et al. |
| 2006/0241570 A1 | 10/2006 | Wilk |
| 2006/0247500 A1 | 11/2006 | Voegele et al. |
| 2006/0247576 A1 | 11/2006 | Poncet |
| 2006/0247663 A1 | 11/2006 | Schwartz et al. |
| 2006/0247673 A1 | 11/2006 | Voegele et al. |
| 2006/0253004 A1 | 11/2006 | Frisch et al. |

(56) References Cited

U.S. PATENT DOCUMENTS

| | | |
|---|---|---|
| 2006/0253039 A1 | 11/2006 | McKenna et al. |
| 2006/0258907 A1 | 11/2006 | Stefanchik et al. |
| 2006/0258908 A1 | 11/2006 | Stefanchik et al. |
| 2006/0258910 A1 | 11/2006 | Stefanchik et al. |
| 2006/0258954 A1 | 11/2006 | Timberlake et al. |
| 2006/0258955 A1 | 11/2006 | Hoffman et al. |
| 2006/0259010 A1 | 11/2006 | Stefanchik et al. |
| 2006/0259073 A1 | 11/2006 | Miyamoto et al. |
| 2006/0264752 A1 | 11/2006 | Rubinsky et al. |
| 2006/0264904 A1 | 11/2006 | Kerby et al. |
| 2006/0264930 A1 | 11/2006 | Nishimura |
| 2006/0270902 A1 | 11/2006 | Igarashi et al. |
| 2006/0271042 A1 | 11/2006 | Latterell et al. |
| 2006/0271102 A1 | 11/2006 | Bosshard et al. |
| 2006/0276835 A1 | 12/2006 | Uchida |
| 2006/0281970 A1 | 12/2006 | Stokes et al. |
| 2006/0282106 A1 | 12/2006 | Cole et al. |
| 2006/0285732 A1 | 12/2006 | Horn et al. |
| 2006/0287644 A1 | 12/2006 | Inganas et al. |
| 2006/0287666 A1 | 12/2006 | Saadat et al. |
| 2006/0293626 A1 | 12/2006 | Byrum et al. |
| 2007/0002135 A1 | 1/2007 | Glukhovsky |
| 2007/0005019 A1 | 1/2007 | Okishige |
| 2007/0010801 A1 | 1/2007 | Chen et al. |
| 2007/0015965 A1 | 1/2007 | Cox et al. |
| 2007/0016225 A1 | 1/2007 | Nakao |
| 2007/0032700 A1 | 2/2007 | Fowler et al. |
| 2007/0032701 A1 | 2/2007 | Fowler et al. |
| 2007/0043261 A1 | 2/2007 | Watanabe et al. |
| 2007/0043345 A1 | 2/2007 | Davalos et al. |
| 2007/0049800 A1 | 3/2007 | Boulais |
| 2007/0049902 A1 | 3/2007 | Griffin et al. |
| 2007/0051375 A1 | 3/2007 | Milliman |
| 2007/0060880 A1 | 3/2007 | Gregorich et al. |
| 2007/0066869 A1 | 3/2007 | Hoffman |
| 2007/0067017 A1 | 3/2007 | Trapp |
| 2007/0073102 A1 | 3/2007 | Matsuno et al. |
| 2007/0073269 A1 | 3/2007 | Becker |
| 2007/0079924 A1 | 4/2007 | Saadat et al. |
| 2007/0083195 A1 | 4/2007 | Werneth et al. |
| 2007/0088370 A1 | 4/2007 | Kahle et al. |
| 2007/0100375 A1 | 5/2007 | Mikkaichi et al. |
| 2007/0100376 A1 | 5/2007 | Mikkaichi et al. |
| 2007/0106118 A1 | 5/2007 | Moriyama |
| 2007/0106317 A1 | 5/2007 | Shelton, IV et al. |
| 2007/0112251 A1 | 5/2007 | Nakhuda |
| 2007/0112331 A1 | 5/2007 | Weber et al. |
| 2007/0112342 A1 | 5/2007 | Pearson et al. |
| 2007/0112383 A1 | 5/2007 | Conlon et al. |
| 2007/0112384 A1 | 5/2007 | Conlon et al. |
| 2007/0112385 A1 | 5/2007 | Conlon |
| 2007/0112417 A1 | 5/2007 | Shanley et al. |
| 2007/0112425 A1 | 5/2007 | Schaller et al. |
| 2007/0118115 A1 | 5/2007 | Artale et al. |
| 2007/0123840 A1 | 5/2007 | Cox |
| 2007/0129605 A1 | 6/2007 | Schaaf |
| 2007/0129719 A1 | 6/2007 | Kendale et al. |
| 2007/0129760 A1 | 6/2007 | Demarais et al. |
| 2007/0135709 A1 | 6/2007 | Rioux et al. |
| 2007/0135803 A1 | 6/2007 | Belson |
| 2007/0142706 A1 | 6/2007 | Matsui et al. |
| 2007/0142710 A1 | 6/2007 | Yokoi et al. |
| 2007/0142780 A1 | 6/2007 | Van Lue |
| 2007/0154460 A1 | 7/2007 | Kraft et al. |
| 2007/0156028 A1 | 7/2007 | Van Lue et al. |
| 2007/0156127 A1 | 7/2007 | Rioux et al. |
| 2007/0161855 A1 | 7/2007 | Mikkaichi et al. |
| 2007/0162101 A1 | 7/2007 | Burgermeister et al. |
| 2007/0167901 A1 | 7/2007 | Herrig et al. |
| 2007/0173691 A1 | 7/2007 | Yokoi et al. |
| 2007/0173869 A1 | 7/2007 | Gannoe et al. |
| 2007/0173870 A2 | 7/2007 | Zacharias |
| 2007/0173872 A1 | 7/2007 | Neuenfeldt |
| 2007/0179525 A1 | 8/2007 | Frecker et al. |
| 2007/0179530 A1 | 8/2007 | Tieu et al. |
| 2007/0197865 A1 | 8/2007 | Miyake et al. |
| 2007/0198057 A1 | 8/2007 | Gelbart et al. |
| 2007/0203398 A1 | 8/2007 | Bonadio et al. |
| 2007/0203487 A1 | 8/2007 | Sugita |
| 2007/0208336 A1 | 9/2007 | Kim et al. |
| 2007/0208364 A1 | 9/2007 | Smith et al. |
| 2007/0208407 A1* | 9/2007 | Gerdts et al. ............... 623/1.11 |
| 2007/0213754 A1 | 9/2007 | Mikkaichi et al. |
| 2007/0225554 A1 | 9/2007 | Maseda et al. |
| 2007/0233040 A1 | 10/2007 | MacNamara et al. |
| 2007/0244358 A1 | 10/2007 | Lee |
| 2007/0244550 A1* | 10/2007 | Eidenschink ............... 623/1.49 |
| 2007/0250036 A1* | 10/2007 | Volk et al. ................... 604/510 |
| 2007/0250038 A1 | 10/2007 | Boulais |
| 2007/0250057 A1 | 10/2007 | Nobis et al. |
| 2007/0255096 A1 | 11/2007 | Stefanchik et al. |
| 2007/0255100 A1 | 11/2007 | Barlow et al. |
| 2007/0255273 A1 | 11/2007 | Fernandez et al. |
| 2007/0255303 A1 | 11/2007 | Bakos et al. |
| 2007/0255306 A1 | 11/2007 | Conlon et al. |
| 2007/0260112 A1 | 11/2007 | Rahmani |
| 2007/0260117 A1 | 11/2007 | Zwolinski et al. |
| 2007/0260121 A1 | 11/2007 | Bakos et al. |
| 2007/0260242 A1 | 11/2007 | Dycus et al. |
| 2007/0260273 A1 | 11/2007 | Cropper et al. |
| 2007/0260302 A1 | 11/2007 | Igaki |
| 2007/0270629 A1 | 11/2007 | Charles |
| 2007/0270889 A1 | 11/2007 | Conlon et al. |
| 2007/0270895 A1 | 11/2007 | Nobis et al. |
| 2007/0270907 A1 | 11/2007 | Stokes et al. |
| 2007/0282165 A1 | 12/2007 | Hopkins et al. |
| 2007/0282371 A1 | 12/2007 | Lee et al. |
| 2007/0293727 A1 | 12/2007 | Goldfarb et al. |
| 2007/0299387 A1 | 12/2007 | Williams et al. |
| 2008/0004650 A1 | 1/2008 | George |
| 2008/0015409 A1 | 1/2008 | Barlow |
| 2008/0015413 A1 | 1/2008 | Barlow et al. |
| 2008/0015552 A1 | 1/2008 | Doyle et al. |
| 2008/0021416 A1 | 1/2008 | Arai et al. |
| 2008/0022927 A1 | 1/2008 | Zhang |
| 2008/0027387 A1 | 1/2008 | Grabinsky |
| 2008/0033451 A1 | 2/2008 | Rieber et al. |
| 2008/0051629 A1 | 2/2008 | Sugiyama et al. |
| 2008/0051735 A1 | 2/2008 | Measamer et al. |
| 2008/0058586 A1 | 3/2008 | Karpiel |
| 2008/0058854 A1 | 3/2008 | Kieturakis et al. |
| 2008/0065169 A1 | 3/2008 | Colliou et al. |
| 2008/0071264 A1 | 3/2008 | Azure |
| 2008/0086172 A1 | 4/2008 | Martin et al. |
| 2008/0097159 A1 | 4/2008 | Ishiguro |
| 2008/0097472 A1 | 4/2008 | Agmon et al. |
| 2008/0097483 A1 | 4/2008 | Ortiz et al. |
| 2008/0103527 A1 | 5/2008 | Martin et al. |
| 2008/0114384 A1 | 5/2008 | Chang et al. |
| 2008/0119870 A1 | 5/2008 | Williams |
| 2008/0119891 A1 | 5/2008 | Miles et al. |
| 2008/0125796 A1 | 5/2008 | Graham |
| 2008/0132892 A1 | 6/2008 | Lunsford et al. |
| 2008/0139882 A1 | 6/2008 | Fujimori |
| 2008/0140069 A1 | 6/2008 | Filloux et al. |
| 2008/0140071 A1 | 6/2008 | Vegesna |
| 2008/0147000 A1* | 6/2008 | Seibel et al. ............... 604/98.01 |
| 2008/0147113 A1 | 6/2008 | Nobis et al. |
| 2008/0171907 A1 | 7/2008 | Long et al. |
| 2008/0177135 A1 | 7/2008 | Muyari et al. |
| 2008/0188710 A1 | 8/2008 | Segawa et al. |
| 2008/0188868 A1 | 8/2008 | Weitzner et al. |
| 2008/0200755 A1 | 8/2008 | Bakos |
| 2008/0200762 A1 | 8/2008 | Stokes et al. |
| 2008/0200911 A1 | 8/2008 | Long |
| 2008/0200933 A1 | 8/2008 | Bakos et al. |
| 2008/0200934 A1 | 8/2008 | Fox |
| 2008/0208213 A1 | 8/2008 | Benjamin et al. |
| 2008/0221587 A1 | 9/2008 | Schwartz |
| 2008/0228213 A1 | 9/2008 | Blakeney et al. |
| 2008/0230972 A1 | 9/2008 | Ganley |
| 2008/0234696 A1 | 9/2008 | Taylor et al. |
| 2008/0243106 A1 | 10/2008 | Coe |
| 2008/0243148 A1 | 10/2008 | Mikkaichi et al. |

(56) References Cited

U.S. PATENT DOCUMENTS

| | | |
|---|---|---|
| 2008/0243176 A1 | 10/2008 | Weitzner |
| 2008/0249567 A1 | 10/2008 | Kaplan |
| 2008/0262513 A1 | 10/2008 | Stahler et al. |
| 2008/0262524 A1 | 10/2008 | Bangera et al. |
| 2008/0262540 A1 | 10/2008 | Bangera et al. |
| 2008/0269782 A1 | 10/2008 | Stefanchik et al. |
| 2008/0269783 A1 | 10/2008 | Griffith |
| 2008/0275474 A1 | 11/2008 | Martin et al. |
| 2008/0275475 A1 | 11/2008 | Schwemberger et al. |
| 2008/0287737 A1 | 11/2008 | Dejima |
| 2008/0287983 A1 | 11/2008 | Smith et al. |
| 2008/0300461 A1 | 12/2008 | Shaw et al. |
| 2008/0300547 A1 | 12/2008 | Bakos |
| 2008/0309758 A1 | 12/2008 | Karasawa et al. |
| 2008/0312496 A1 | 12/2008 | Zwolinski |
| 2008/0312499 A1 | 12/2008 | Handa et al. |
| 2008/0312500 A1 | 12/2008 | Asada et al. |
| 2008/0312506 A1 | 12/2008 | Spivey et al. |
| 2008/0319436 A1 | 12/2008 | Daniel et al. |
| 2008/0319439 A1 | 12/2008 | Ootsubu |
| 2009/0005636 A1 | 1/2009 | Pang et al. |
| 2009/0054728 A1 | 2/2009 | Trusty |
| 2009/0062788 A1 | 3/2009 | Long et al. |
| 2009/0062792 A1 | 3/2009 | Vakharia et al. |
| 2009/0062795 A1 | 3/2009 | Vakharia et al. |
| 2009/0069634 A1 | 3/2009 | Larkin |
| 2009/0076499 A1 | 3/2009 | Azure |
| 2009/0078736 A1 | 3/2009 | Van Lue |
| 2009/0082776 A1 | 3/2009 | Cresina |
| 2009/0082779 A1 | 3/2009 | Nakao |
| 2009/0112059 A1 | 4/2009 | Nobis |
| 2009/0112062 A1 | 4/2009 | Bakos |
| 2009/0112063 A1 | 4/2009 | Bakos et al. |
| 2009/0125042 A1 | 5/2009 | Mouw |
| 2009/0131751 A1 | 5/2009 | Spivey et al. |
| 2009/0131932 A1 | 5/2009 | Vakharia et al. |
| 2009/0131933 A1 | 5/2009 | Ghabrial et al. |
| 2009/0143639 A1 | 6/2009 | Stark |
| 2009/0143649 A1 | 6/2009 | Rossi |
| 2009/0143794 A1 | 6/2009 | Conlon et al. |
| 2009/0143818 A1 | 6/2009 | Faller et al. |
| 2009/0149710 A1 | 6/2009 | Stefanchik et al. |
| 2009/0177031 A1 | 7/2009 | Surti et al. |
| 2009/0177219 A1 | 7/2009 | Conlon |
| 2009/0182332 A1 | 7/2009 | Long et al. |
| 2009/0192344 A1 | 7/2009 | Bakos et al. |
| 2009/0192534 A1 | 7/2009 | Ortiz et al. |
| 2009/0198231 A1 | 8/2009 | Esser et al. |
| 2009/0198253 A1 | 8/2009 | Omori |
| 2009/0210000 A1 | 8/2009 | Sullivan et al. |
| 2009/0216248 A1 | 8/2009 | Uenohara et al. |
| 2009/0221873 A1 | 9/2009 | McGrath |
| 2009/0227828 A1 | 9/2009 | Swain et al. |
| 2009/0228001 A1 | 9/2009 | Pacey |
| 2009/0248055 A1 | 10/2009 | Spivey et al. |
| 2009/0259105 A1 | 10/2009 | Miyano et al. |
| 2009/0269317 A1 | 10/2009 | Davalos |
| 2009/0281559 A1 | 11/2009 | Swain et al. |
| 2009/0287206 A1 | 11/2009 | Jun |
| 2009/0287236 A1 | 11/2009 | Bakos et al. |
| 2009/0292164 A1 | 11/2009 | Yamatani |
| 2009/0299135 A1 | 12/2009 | Spivey |
| 2009/0299143 A1 | 12/2009 | Conlon et al. |
| 2009/0299362 A1 | 12/2009 | Long et al. |
| 2009/0299385 A1 | 12/2009 | Stefanchik et al. |
| 2009/0299406 A1 | 12/2009 | Swain et al. |
| 2009/0299409 A1 | 12/2009 | Coe et al. |
| 2009/0306658 A1 | 12/2009 | Nobis et al. |
| 2009/0306683 A1 | 12/2009 | Zwolinski et al. |
| 2009/0322864 A1 | 12/2009 | Karasawa et al. |
| 2009/0326332 A1 | 12/2009 | Carter |
| 2009/0326561 A1 | 12/2009 | Carroll, II et al. |
| 2010/0010294 A1 | 1/2010 | Conlon et al. |
| 2010/0010298 A1 | 1/2010 | Bakos et al. |
| 2010/0010299 A1 | 1/2010 | Bakos et al. |
| 2010/0010303 A1 | 1/2010 | Bakos |
| 2010/0010510 A1 | 1/2010 | Stefanchik |
| 2010/0010511 A1 | 1/2010 | Harris et al. |
| 2010/0023032 A1 | 1/2010 | Granja Filho |
| 2010/0030211 A1 | 2/2010 | Davalos et al. |
| 2010/0036198 A1 | 2/2010 | Tacchino et al. |
| 2010/0042045 A1 | 2/2010 | Spivey |
| 2010/0048990 A1 | 2/2010 | Bakos |
| 2010/0049190 A1 | 2/2010 | Long et al. |
| 2010/0049223 A1 | 2/2010 | Granja Filho |
| 2010/0056861 A1 | 3/2010 | Spivey |
| 2010/0056862 A1 | 3/2010 | Bakos |
| 2010/0056864 A1 | 3/2010 | Lee |
| 2010/0057085 A1 | 3/2010 | Holcomb et al. |
| 2010/0057108 A1 | 3/2010 | Spivey et al. |
| 2010/0063538 A1 | 3/2010 | Spivey et al. |
| 2010/0076451 A1 | 3/2010 | Zwolinski et al. |
| 2010/0076460 A1 | 3/2010 | Taylor et al. |
| 2010/0081877 A1 | 4/2010 | Vakharia |
| 2010/0091128 A1 | 4/2010 | Ogasawara et al. |
| 2010/0113872 A1 | 5/2010 | Asada et al. |
| 2010/0121362 A1 | 5/2010 | Clague et al. |
| 2010/0130817 A1 | 5/2010 | Conlon |
| 2010/0130975 A1 | 5/2010 | Long |
| 2010/0131005 A1 | 5/2010 | Conlon |
| 2010/0152539 A1 | 6/2010 | Ghabrial et al. |
| 2010/0152609 A1 | 6/2010 | Zwolinski et al. |
| 2010/0152746 A1 | 6/2010 | Ceniccola et al. |
| 2010/0179510 A1 | 7/2010 | Fox et al. |
| 2010/0179530 A1 | 7/2010 | Long et al. |
| 2010/0191050 A1 | 7/2010 | Zwolinski |
| 2010/0191267 A1 | 7/2010 | Fox |
| 2010/0198005 A1 | 8/2010 | Fox |
| 2010/0198149 A1 | 8/2010 | Fox |
| 2010/0198248 A1 | 8/2010 | Vakharia |
| 2010/0217367 A1 | 8/2010 | Belson |
| 2010/0249700 A1 | 9/2010 | Spivey |
| 2010/0261994 A1 | 10/2010 | Davalos et al. |
| 2010/0286791 A1 | 11/2010 | Goldsmith |
| 2010/0298642 A1 | 11/2010 | Trusty et al. |
| 2010/0312056 A1 | 12/2010 | Galperin et al. |
| 2010/0331622 A2 | 12/2010 | Conlon |
| 2010/0331758 A1 | 12/2010 | Davalos et al. |
| 2010/0331774 A2 | 12/2010 | Spivey |
| 2011/0077476 A1 | 3/2011 | Rofougaran |
| 2011/0093009 A1 | 4/2011 | Fox |
| 2011/0098694 A1 | 4/2011 | Long |
| 2011/0098704 A1 | 4/2011 | Long et al. |
| 2011/0105850 A1 | 5/2011 | Voegele et al. |
| 2011/0106221 A1 | 5/2011 | Neal, II et al. |
| 2011/0112434 A1 | 5/2011 | Ghabrial et al. |
| 2011/0115891 A1 | 5/2011 | Trusty |
| 2011/0124964 A1 | 5/2011 | Nobis |
| 2011/0152609 A1 | 6/2011 | Trusty et al. |
| 2011/0152610 A1 | 6/2011 | Trusty et al. |
| 2011/0152612 A1 | 6/2011 | Trusty et al. |
| 2011/0152858 A1 | 6/2011 | Long et al. |
| 2011/0152859 A1 | 6/2011 | Long et al. |
| 2011/0152878 A1 | 6/2011 | Trusty et al. |
| 2011/0152923 A1 | 6/2011 | Fox |
| 2011/0160514 A1 | 6/2011 | Long et al. |
| 2011/0190659 A1 | 8/2011 | Long et al. |
| 2011/0190764 A1 | 8/2011 | Long et al. |
| 2011/0193948 A1 | 8/2011 | Amling et al. |
| 2011/0245619 A1 | 10/2011 | Holcomb |
| 2011/0285488 A1 | 11/2011 | Scott et al. |
| 2011/0306971 A1 | 12/2011 | Long |
| 2012/0004502 A1 | 1/2012 | Weitzner et al. |
| 2012/0029335 A1 | 2/2012 | Sudam et al. |
| 2012/0088965 A1 | 4/2012 | Stokes et al. |
| 2012/0089089 A1 | 4/2012 | Swain et al. |
| 2012/0089093 A1 | 4/2012 | Trusty |
| 2012/0116155 A1 | 5/2012 | Trusty |
| 2012/0179148 A1 | 7/2012 | Conlon |
| 2012/0191075 A1 | 7/2012 | Trusty |
| 2012/0220998 A1 | 8/2012 | Long et al. |
| 2012/0220999 A1 | 8/2012 | Long |
| 2012/0221002 A1 | 8/2012 | Long et al. |

(56) References Cited

U.S. PATENT DOCUMENTS

| | | |
|---|---|---|
| 2012/0238796 A1 | 9/2012 | Conlon |
| 2012/0330306 A1 | 12/2012 | Long et al. |
| 2013/0090666 A1 | 4/2013 | Hess et al. |

FOREIGN PATENT DOCUMENTS

| | | |
|---|---|---|
| DE | 4323585 A1 | 1/1995 |
| DE | 19713797 A1 | 10/1997 |
| DE | 19757056 B4 | 8/2008 |
| DE | 102006027873 B4 | 10/2009 |
| EP | 0086338 A1 | 8/1983 |
| EP | 0286415 A2 | 10/1988 |
| EP | 0589454 A2 | 3/1994 |
| EP | 0464479 B1 | 3/1995 |
| EP | 0529675 B1 | 2/1996 |
| EP | 0621009 B1 | 7/1997 |
| EP | 0724863 B1 | 7/1999 |
| EP | 0760629 B1 | 11/1999 |
| EP | 0818974 B1 | 7/2001 |
| EP | 1281356 A2 | 2/2003 |
| EP | 0947166 B1 | 5/2003 |
| EP | 0836832 B1 | 12/2003 |
| EP | 1402837 A1 | 3/2004 |
| EP | 0744918 B1 | 4/2004 |
| EP | 0931515 B1 | 8/2004 |
| EP | 0941128 B1 | 10/2004 |
| EP | 1411843 B1 | 10/2004 |
| EP | 1150614 B1 | 11/2004 |
| EP | 1477104 A1 | 11/2004 |
| EP | 1481642 A1 | 12/2004 |
| EP | 1493391 A1 | 1/2005 |
| EP | 0848598 B1 | 2/2005 |
| EP | 1281360 B1 | 3/2005 |
| EP | 1568330 A1 | 8/2005 |
| EP | 1452143 81 | 9/2005 |
| EP | 1616527 A2 | 1/2006 |
| EP | 1006888 B1 | 3/2006 |
| EP | 1629764 A1 | 3/2006 |
| EP | 1013229 B1 | 6/2006 |
| EP | 1721561 A1 | 11/2006 |
| EP | 1153578 B1 | 3/2007 |
| EP | 1334696 B1 | 3/2007 |
| EP | 1769766 A1 | 4/2007 |
| EP | 1836971 A2 | 9/2007 |
| EP | 1836980 A1 | 9/2007 |
| EP | 1854421 A2 | 11/2007 |
| EP | 1857061 A1 | 11/2007 |
| EP | 1875876 A1 | 1/2008 |
| EP | 1891881 A1 | 2/2008 |
| EP | 1902663 A1 | 3/2008 |
| EP | 1477106 B1 | 6/2008 |
| EP | 1949844 A1 | 7/2008 |
| EP | 1518499 81 | 8/2008 |
| EP | 1582138 B1 | 9/2008 |
| EP | 1709918 B1 | 10/2008 |
| EP | 1985226 A2 | 10/2008 |
| EP | 1994904 A1 | 11/2008 |
| EP | 1707130 B1 | 12/2008 |
| EP | 0723462 B1 | 3/2009 |
| EP | 1769749 B1 | 11/2009 |
| EP | 2135545 A2 | 12/2009 |
| EP | 1493397 81 | 9/2011 |
| FR | 2731610 A1 | 9/1996 |
| GB | 330629 A | 6/1930 |
| GB | 2335860 A | 10/1999 |
| GB | 2403909 A | 1/2005 |
| GB | 2421190 A | 6/2006 |
| GB | 2443261 A | 4/2008 |
| JP | 56-46674 | 4/1981 |
| JP | 63309252 A | 12/1988 |
| JP | 4038960 A | 2/1992 |
| JP | 8-29699 A | 2/1996 |
| JP | 2000245683 A | 9/2000 |
| JP | 2002-369791 A | 12/2002 |
| JP | 2003-088494 A1 | 3/2003 |
| JP | 2003-235852 A | 8/2003 |
| JP | 2004-33525 A | 2/2004 |
| JP | 2004-065745 A | 3/2004 |
| JP | 2005-121947 A | 5/2005 |
| JP | 2005-261514 A | 9/2005 |
| JP | 2006297005 A | 11/2006 |
| JP | 2006-343510 A | 12/2006 |
| NL | 1021295 C2 | 2/2004 |
| SU | 194230 | 5/1967 |
| SU | 980703 | 12/1982 |
| WO | WO 84/01707 A1 | 5/1984 |
| WO | WO 92/13494 A1 | 8/1992 |
| WO | WO 93/10850 A1 | 6/1993 |
| WO | WO 93/20760 A1 | 10/1993 |
| WO | WO 93/20765 A1 | 10/1993 |
| WO | WO 95/09666 A1 | 4/1995 |
| WO | WO 96/22056 A1 | 7/1996 |
| WO | WO 96/27331 A1 | 9/1996 |
| WO | WO 96/39946 A1 | 12/1996 |
| WO | WO 97/12557 A1 | 4/1997 |
| WO | WO 98/01080 A1 | 1/1998 |
| WO | WO 99/00060 A1 | 1/1999 |
| WO | WO 99/09919 A1 | 3/1999 |
| WO | WO 99/17661 A1 | 4/1999 |
| WO | WO 99/30622 A2 | 6/1999 |
| WO | WO 00/35358 A1 | 6/2000 |
| WO | WO 00/68665 A1 | 11/2000 |
| WO | WO 01/10319 A1 | 2/2001 |
| WO | WO 01/26708 A1 | 4/2001 |
| WO | WO 01/41627 A2 | 6/2001 |
| WO | WO 01/58360 A2 | 8/2001 |
| WO | WO 02/11621 A2 | 2/2002 |
| WO | WO 02/34122 A2 | 5/2002 |
| WO | WO 02/094082 A2 | 11/2002 |
| WO | WO 03/045260 A1 | 6/2003 |
| WO | WO 03/047684 A2 | 6/2003 |
| WO | WO 03/059412 A2 | 7/2003 |
| WO | WO 03/078721 A2 | 9/2003 |
| WO | WO 03/081761 A2 | 10/2003 |
| WO | WO 03/082129 A2 | 10/2003 |
| WO | WO 2004/006789 A1 | 1/2004 |
| WO | WO 2004/028613 A2 | 4/2004 |
| WO | WO 2004/037123 A1 | 5/2004 |
| WO | WO 2004/037149 A1 | 5/2004 |
| WO | WO 2004/052221 A1 | 6/2004 |
| WO | WO 2004/086984 A1 | 10/2004 |
| WO | WO 2005/009211 A2 | 2/2005 |
| WO | WO 2005/018467 A2 | 3/2005 |
| WO | WO 2005/037088 A2 | 4/2005 |
| WO | WO 2005/048827 A1 | 6/2005 |
| WO | WO 2005/065284 A2 | 7/2005 |
| WO | WO 2005/097019 A2 | 10/2005 |
| WO | WO 2005/097234 A2 | 10/2005 |
| WO | WO 2005/112810 A2 | 12/2005 |
| WO | WO 2005/120363 A1 | 12/2005 |
| WO | WO 2005/122866 A1 | 12/2005 |
| WO | WO 2006/007399 A1 | 1/2006 |
| WO | WO 2006/012630 A2 | 2/2006 |
| WO | WO 2006/040109 A1 | 4/2006 |
| WO | WO 2006/041881 A2 | 4/2006 |
| WO | WO 2006/060405 A2 | 6/2006 |
| WO | WO 2006/110733 A2 | 10/2006 |
| WO | WO 2006/113216 A2 | 10/2006 |
| WO | WO 2007/013059 A2 | 2/2007 |
| WO | WO 2007/014063 A2 | 2/2007 |
| WO | WO 2007/048085 A2 | 4/2007 |
| WO | WO 2007/063550 A2 | 6/2007 |
| WO | WO 2007/100067 A1 | 9/2007 |
| WO | WO 2007/109171 A2 | 9/2007 |
| WO | WO 2007/135577 A2 | 11/2007 |
| WO | WO 2007/143200 A2 | 12/2007 |
| WO | WO 2007/144004 A1 | 12/2007 |
| WO | WO 2008/005433 A1 | 1/2008 |
| WO | WO 2008/033356 A2 | 3/2008 |
| WO | WO 2008/041225 A2 | 4/2008 |
| WO | WO 2008/076337 A1 | 6/2008 |
| WO | WO 2008/076800 A2 | 6/2008 |
| WO | WO 2008/079440 A2 | 7/2008 |
| WO | WO 2008/101075 A2 | 8/2008 |

(56) References Cited

FOREIGN PATENT DOCUMENTS

| WO | WO 2008/102154 A2 | 8/2008 |
|---|---|---|
| WO | WO 2008/108863 A2 | 9/2008 |
| WO | WO 2008/151237 A1 | 12/2008 |
| WO | WO 2009/021030 A1 | 2/2009 |
| WO | WO 2009/027065 A1 | 3/2009 |
| WO | WO 2009/029065 A1 | 3/2009 |
| WO | WO 2009/032623 A2 | 3/2009 |
| WO | WO 2009/036457 A1 | 3/2009 |
| WO | WO 2009/121017 A1 | 10/2009 |
| WO | WO 2010/027688 A1 | 3/2010 |
| WO | WO 2010/056716 A2 | 5/2010 |
| WO | WO 2010/080974 A1 | 7/2010 |
| WO | WO 2010/088481 A1 | 8/2010 |

OTHER PUBLICATIONS

Ethicon, Inc., "Wound Closure Manual: Chapter 3 (The Surgical Needle)," 15 pages, (1994).
Guido M. Sclabas, M.D., et al., "Endoluminal Methods for Gastrotomy Closure in Natural Orifice TransEnteric Surgery (NOTES)," Surgical Innovation, vol. 13, No. 1, pp. 23-30, Mar. 2006.
Fritscher-Ravens, et al., "Transgastric Gastropexy and Hiatal Hernia Repair for GERD Under EUS Control: a Porcine Model," Gastrointestinal Endoscopy, vol. 59, No. 1, pp. 89-95, 2004.
Ogando, "Prototype Tools That Go With the Flow," Design News, 2 pages, Jul. 17, 2006.
Edd, et al., "In Vivo Results of a New Focal Tissue Ablation Technique: Irreversible Electroporation," IEEE Trans Biomed Eng, vol. 53, pp. 1409-1415, 2006.
Kennedy, et al., "High-Burst-Strength, Feedback-Controlled Bipolar Vessel Sealing," Surgical Endoscopy, vol. 12, pp. 876-878 (1998).
Collins et al., "Local Gene Therapy of Solid Tumors with GM-CSF and B7-1 Eradicates Both Treated and Distal Tumors," Cancer Gene Therapy, vol. 13, pp. 1061-1071 (2006).
K. Sumiyama et al., "Transesophageal Mediastinoscopy by Submucosal Endoscopy With Mucosal Flap Safety Value Technique," Gastrointest Endosc., Apr. 2007, vol. 65(4), pp. 679-683 (Abstract).
K. Sumiyama et al., "Submucosal Endoscopy with Mucosal Flap Safety Valve," Gastrointest Endosc. Apr. 2007, vol. 65(4) pp. 694-695 (Abstract).
K. Sumiyama et al., "Transgastric Cholecystectomy: Transgastric Accessibility to the Gallbladder Improved with the SEMF Method and a Novel Multibending Therapeutic Endoscope," Gastrointest Endosc., Jun. 2007, vol. 65(7), pp. 1028-1034 (Abstract).
K. Sumiyama et al., "Endoscopic Caps," Tech. Gastrointest. Endosc., vol. 8, pp. 28-32, 2006.
"Z-Offset Technique Used in the Introduction of Trocar During Laparoscopic Surgery," M.S. Hershey NOTES Presentation to EES NOTES Development Team, Sep. 27, 2007.
F.N. Denans, Nouveau Procede Pour La Guerison Des Plaies Des Intestines, Extrait Des Seances De La Societe Royale De Medecine De Marseille, Pendant Le Mois De Decembre 1825, et le Premier Tremestre De 1826, Séance Du 24 Fevrier 1826. Recueil De La Societe Royale De Medecin De Marseille. Marseille: Impr. D'Achard, 1826; 1:127-31. (with English translation).
I. Fraser, "An Historical Perspective on Mechanical Aids in Intestinal Anastomosis," Surg, Gynecol. Obstet. (Oct. 1982), vol. 155, pp. 566-574.
M.E. Ryan et al., "Endoscopic Intervention for Biliary Leaks After Laparoscopic Cholecystectomy: A Multicenter Review," Gastrointest. Endosc., vol. 47(3), 1998, pp. 261-266.
C. Cope, "Creation of Compression Gastroenterostomy by Means of the Oral, Percutaneous, or Surgical Introduction of Magnets: Feasibility Study in Swine," J. Vasc Intery Radiol, (1995), vol. 6(4), pp, 539-545.
J.W. Hazey et al., "Natural Orifice Transgastric Endoscopic Peritoneoscopy in Humans: Initial Clinical Trial," Surg Endosc, (Jan. 2008), vol. 22(1), pp. 16-20.

N. Chopita et al., "Endoscopic Gastroenteric Anastamosis Using Magnets," Endoscopy, (2005), vol. 37(4), pp. 313-317.
C. Cope et al., "Long Term Patency of Experimental Magnetic Compression Gastroenteric Anastomoses Achieved with Covered Stents," Gastrointest Endosc, (2001), vol. 53, pp. 780-784.
H. Okajima et al., "Magnet Compression Anastamosis for Bile Duct Stenosis After Duct to Duct Biliary Reconstruction in Living Donor Liver Transplantation," Liver Transplantation (2005), pp. 473-475.
A. Fritscher-Ravens et al., "Transluminal Endosurgery: Single Lumen Access Anastamotic Device for Flexible Endoscopy," Gastrointestinal Endosc, (2003), vol. 58(4), pp. 585-591.
G.A. Hallenbeck, M.D. et al., "An Instrument for Colorectal Anastomosis Without Sutrues," Dis Col Rectum, (1963), vol. 5, pp. 98-101.
T. Hardy, Jr., M.D. et al., "A Biofragmentable Ring for Sutureless Bowel Anastomosis. An Experimental Study," Dis Col Rectum, (1985), vol. 28, pp. 484-490.
P. O'Neill, M.D. et al., "Nonsuture Intestinal Anastomosis," Am J. Surg, (1962), vol. 104, pp. 761-767.
C.P. Swain, M.D. et al., "Anastomosis at Flexible Endoscopy: An Experimental Study of Compression Button Gastrojejunostomy," Gastrointest Endosc, (1991), vol. 37, pp. 628-632.
J.B. Murphy, M.D., "Cholecysto-Intestinal, Gastro-Intestinal, Entero-Intestinal Anastomosis, and Approximation Without Sutures (original research)," Med Rec, (Dec. 10, 1892), vol. 42(24), pp. 665-676.
USCI® EndoSurgical Operating System—g-Prox® Tissue Grasper/Approximation Device; [online] URL: http://www.usgimedical.com/eos/components-gprox.htm—accessed May 30, 2008 (2 pages).
Printout of web page—http://www.vacumed.com/zcom/product/Product.do?compid=27&prodid=852, #51XX Low-Cost Permanent Tubes 2MM ID, Smooth Interior Walls, VacuMed, Ventura, California, Accessed Jul. 24, 2007.
Endoscopic Retrograde Cholangiopancreatogram (ERCP); [online] URL: http://www.webmd.com/digestive-disorders/endoscopic-retrograde-cholangiopancreatogram-ercp.htm; last updated: Apr. 30, 2007; accessed: Feb. 21, 2008 (6 pages).
ERCP; Jackson Siegelbaum Gastroenterology; [online] URL: http://www.gicare.com/pated/epdgs20.htm; accessed Feb. 21, 2008 (3 pages).
D.G. Fong et al., "Transcolonic Ventral Wall Hernia Mesh Fixation in a Porcine Model," Endoscopy 2007; 39: 865-869.
B. Rubinsky, Ph.D., "Irreversible Electroporation in Medicine," Technology in Cancer Research and Treatment, vol. 6, No. 4, Aug. (2007), pp. 255-259.
D.B. Nelson, MD et al., "Endoscopic Hemostatic Devices," Gastrointestinal Endoscopy, vol. 54, No. 6, 2001, pp. 833-840.
CRE™ Pulmonary Balloon Dilator; [online] URL: http://www.bostonscientific.com/Device.bsci?page=HCP_Overview&navRelId=1000.1003&method=D . . . , accessed Jul. 18, 2008 (4 pages).
J.D. Paulson, M.D., et al., "Development of Flexible Culdoscopy," The Journal of the American Association of Gynecologic Laparoscopists, Nov. 1999, vol. 6, No. 4, pp. 487-490.
H. Seifert, et al., "Retroperitoneal Endoscopic Debridement for Infected Peripancreatic Necrosis," The Lancet, Research Letters, vol. 356, Aug. 19, 2000, pp. 653-655.
K.E. Mönkemüller, M.D., et al., "Transmural Drainage of Pancreatic Fluid Collections Without Electrocautery Using the Seldinger Technique," Gastrointestinal Endoscopy, vol. 48, No. 2, 1998, pp. 195-200, (Accepted Mar. 31, 1998).
D. Wilhelm et al., "An Innovative, Safe and Sterile Sigmoid Access (ISSA) for Notes," Endoscopy 2007, vol. 39, pp. 401-406.
Nakazawa et al., "Radiofrequency Ablation of Hepatocellular Carcinoma: Correlation Between Local Tumor Progression After Ablation and Ablative Margin," AJR, 188, pp. 480-488 (Feb. 2007).
Miklavčič et al., "A validated model of in vivo electric field distribution in tissues for electrochemotherapy and for DNA electrotransfer for gene therapy," Biochimica et Biophysica Acta, 1523, pp. 73-83 (2000).
Evans, "Ablative and cathether-delivered therapies for colorectal liver metastases (CRLM)," EJSO, 33, pp. S64-S75 (2007).
Wong et al., "Combined Percutaneous Radiofrequency Ablation and Ethanol Injection for Hepatocellular Carcinoma in High-Risk Locations," AJR, 190, pp. W187-W195 (2008).

(56) References Cited

OTHER PUBLICATIONS

Heller et al., "Electrically mediated plasmid DNA delivery to hepatocellular carcinomas in vivo," Gene Therapy, 7, pp. 826-829 (2000).
Widera et al., "Increased DNA Vaccine Delivery and Immunogenicity by Electroporation In Vivo," The Journal of Immunology, 164, pp. 4635-4640 (2000).
Weaver et al., "Theory of electroporation: A review," Bioelectrochemistry and Bioenergetics, 41, pp. 135-160 (1996).
Mulier et al., "Radiofrequency Ablation Versus Resection for Resectable Colorectal Liver Metastases: Time for a Randomized Trial?" Annals of Surgical Oncology, 15(1), pp. 144-157 (2008).
Link et al., "Regional Chemotherapy of Nonresectable Colorectal Liver Metastases with Mitoxanthrone, 5-Fluorouracil, Folinic Acid, and Mitomycin C May Prolong Survival," Cancer, 92, pp. 2746-2753 (2001).
Guyton et al., "Membrane Potentials and Action Potentials," W.B. Sanders, ed. Textbook of Medical Physiology, p. 56 (2000).
Guyton et al., "Contraction of Skeletal Muscle," Textbook of Medical Physiology, pp. 82-84 (2000).
"Ethicon Endo-Surgery Novel Investigational Notes and SSL Devices Featured in 15 Presentations at Sages," Apr. 22, 2009 Press Release; URL http://www.jnj.com/connect/news/a11/20090422_152000; accessed Aug. 28, 2009 (3 pages).
"Ethicon Endo-Surgery Studies Presented at DDW Demonstrate Potential of Pure NOTES Surgery With Company's Toolbox," Jun. 3, 2009 Press Release; URL http://www.jnj.com/connect/news/product/20090603_120000; accessed Aug. 28, 2009 (3 pages).
Castellvi et al., "Hybrid Transvaginal NOTES Sleeve Gastrectomy in a Porcine Model Using a Magnetically Anchored Camera and Novel Instrumentation," Abstract submitted along with Poster at SAGES Annual Meeting in Phoenix, AZ, Apr. 22, 2009 (1 page).
Castellvi et al., "Hybrid Transvaginal NOTES Sleeve Gastrectomy in a Porcine Model Using a Magnetically Anchored Camera and Novel Instrumentation," Poster submitted along with Abstract at SAGES Annual Meeting in Phoenix, AZ, Apr. 22, 2009 (1 page).
OCTO Port Modular Laparoscopy System for Single Incision Access, Jan. 4, 2010; UR: http://www.medgadget.com/archives/2010/01/octo_port_modulariaparo . . . ; accessed Jan. 5, 2010 (4 pages).
Hakko Retractors, obtained Aug. 25, 2009 (5 pages).
Zadno et al., "Linear Superelasticity in Cold-Worked Ni—Ti," Engineering Aspects of Shape Memory Alloys, pp. 414-419 (1990).
U.S. Appl. No. 13/013,131, filed Jan. 25, 2011.
U.S. Appl. No. 12/900,132, filed Oct. 7, 2010.
U.S. Appl. No. 12/939,441, filed Nov. 4, 2010.
U.S. Appl. No. 12/902,531, filed Oct. 12, 2010.
U.S. Appl. No. 12/902,550, filed Oct. 12, 2010.
U.S. Appl. No. 13/036,895, filed Feb. 28, 2011.
U.S. Appl. No. 13/036,908, filed Feb. 28, 2011.
U.S. Appl. No. 13/218,221, filed Aug. 25, 2011.
U.S. Appl. No. 13/267,251, filed Oct. 6, 2011.
How Stuff Works "How Smart Structures Will Work," http://science.howstuffworks.com/engineering/structural/smart-structure1.htm; accessed online Nov. 1, 2011 (3 pages).
Instant Armor: Science Videos—Science News—ScienCentral; http://www.sciencentral.com/articles./view.php3?article_id=218392121; accessed online Nov. 1, 2011 (2 pages).
Stanway, Smart Fluids: Current and Future Developments. Material Science and Technology, 20, pp. 931-939, 2004; accessed online Nov. 1, 2011 at http://www.dynamics.group.shef.ac.uk/smart/smart.html (7 pages).
Jolly et al., Properties and Applications of Commercial Magnetorheological Fluids. SPIE 5th Annual Int. Symposium on Smart Structures and Materials, 1998 (18 pages).
Rutala et al. "Guideline for Disinfection and Sterilization in Healthcare Facilities, 2008" (available at http://www.cdc.gov/hicpac/Disinfection_Sterilization/13_11sterilizingPractices.html).
U.S. Appl. No. 13/325,791, filed Dec. 14, 2011.
U.S. Appl. No. 13/399,358, filed Feb. 17, 2012.
U.S. Appl. No. 13/420,818, filed Mar. 15, 2012.
International Search Report for PCT/US2012/021532, dated Jul. 6, 2012 (4 pages).
Bewlay et al., "Spinning" in ASM Handbook, vol. 14B, Metalworking: Sheet Forming (2006).

\* cited by examiner

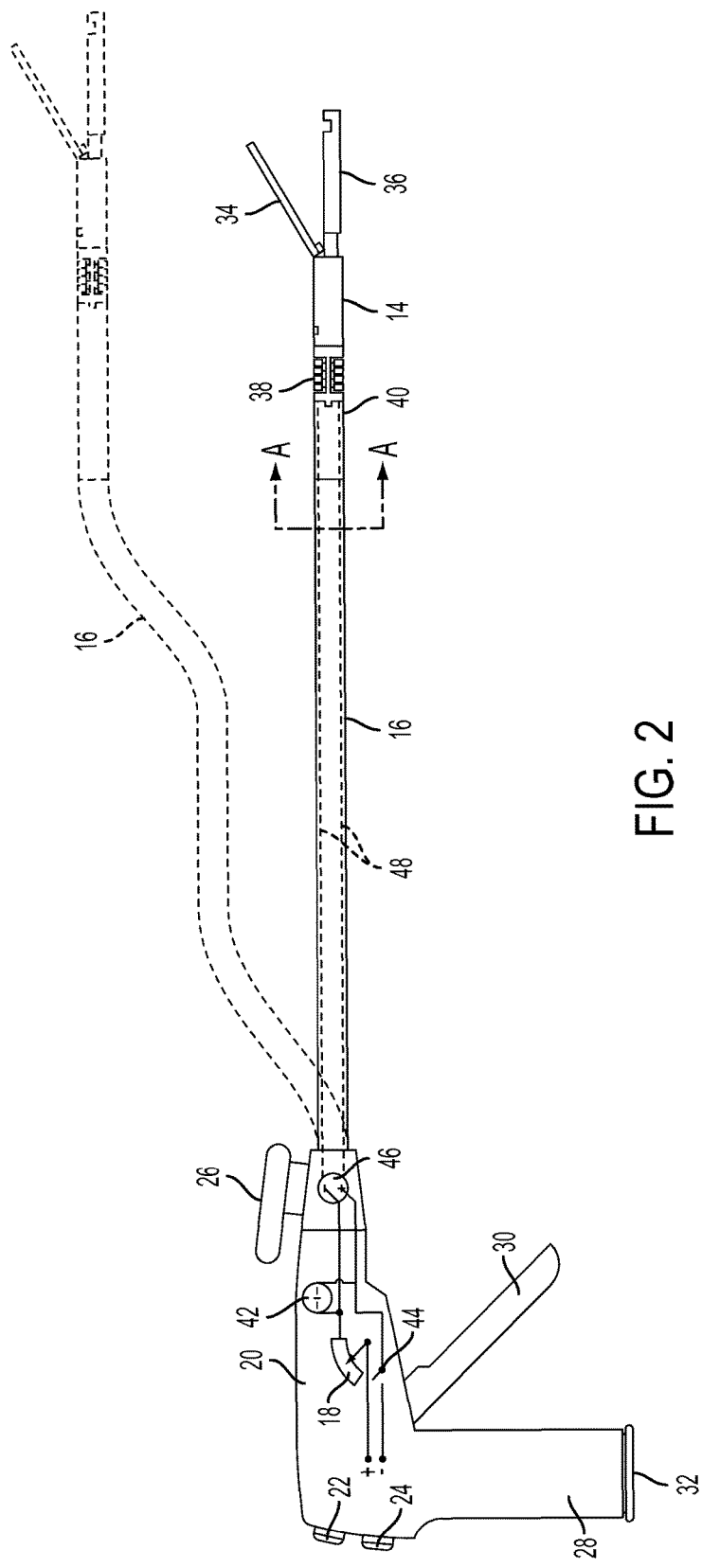
FIG. 2
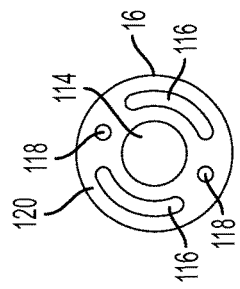
FIG. 4A-A
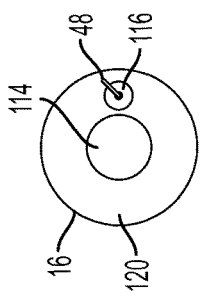
FIG. 3A-A

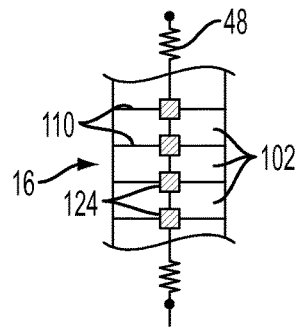
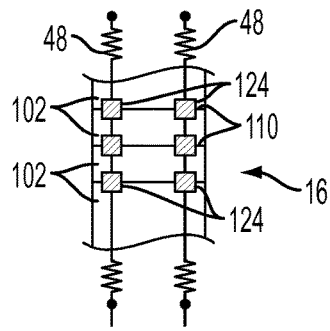
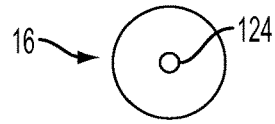
FIG. 14A
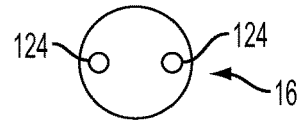
FIG. 14B
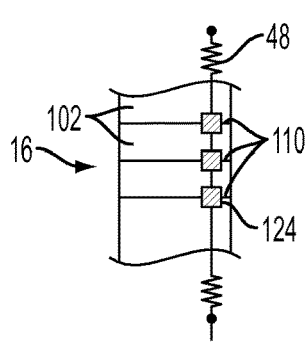
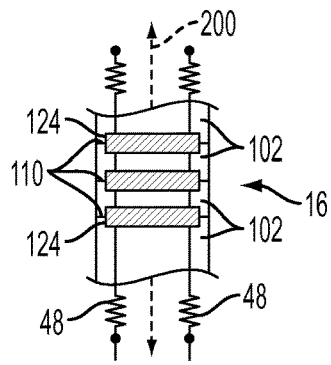
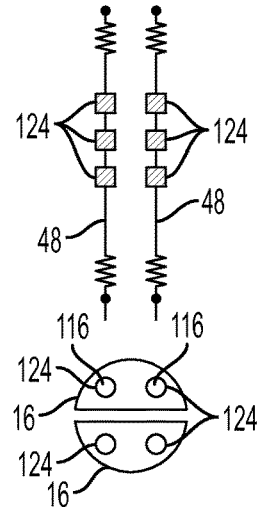
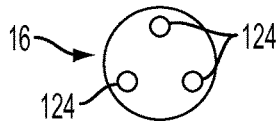
FIG. 14C
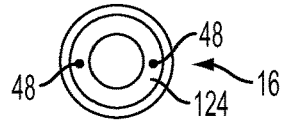
FIG. 14D
FIG. 14E
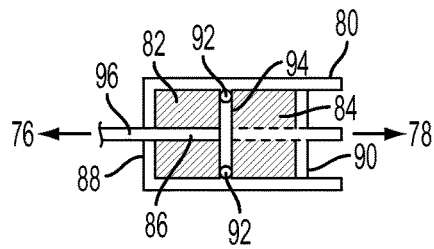
FIG. 15
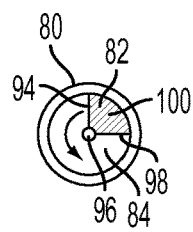
FIG. 16

SURGICAL INSTRUMENT WITH SELECTIVELY RIGIDIZABLE FEATURES

BACKGROUND i. Field of the Invention

The present application relates to methods and devices for minimally invasive surgical procedures and, more particularly, to surgical and diagnostic instruments having selectively rigidizable components.

ii. Description of the Related Art

In minimally invasive surgical and diagnostic procedures, such as laparoscopic surgery, a surgeon may place one or more small ports into a patient's abdomen to gain access into the abdominal cavity of the patient. A surgeon may use, for example, a port for insufflating the abdominal cavity to create space, a port for introducing a laparoscope for viewing, and a number of other ports for introducing surgical instruments for operating on tissue. Other minimally invasive surgical procedures include natural orifice transluminal endoscopic surgery (NOTES) wherein surgical instruments and viewing devices are introduced into a patient's body through, for example, the mouth, nose, vagina, or rectum. The benefits of minimally invasive procedures compared to open surgery procedures for treating certain types of wounds and diseases or for diagnosing certain types of conditions, are now well-known to include faster recovery time and less pain for the patient, better outcomes, and lower overall costs.

In many case, the site of interest in an internal cavity or lumen of a patient is remote from the entry port or natural orifice and an instrument having a long shaft leading from the external entry port or natural orifice to the site of interest is required. The shaft in many cases has to be flexible to allow it to be maneuvered from the port or orifice to the site of interest. That flexibility can, however, make operation of the tool at the end of the shaft, generally referred to as an end effector, difficult.

The foregoing discussion is intended only to illustrate various aspects of the related art in the field of the invention at the time, and should not be taken as a disavowal of claim scope.

SUMMARY

The use of shape altering materials to facilitate the desired functioning of various portions of instruments, such as surgical or diagnostic instruments, is described herein. In various embodiments, a shaft assembly is provided that includes a shaft, at least one cell defined within the shaft, a shape altering material contained within the at least one cell, and, an activation link operatively connectable to a source of activation energy for delivering activation energy to the at least one cell for activating the shape altering material to selectively rigidize or unrigidize the shaft.

In various embodiments, an actuator for producing work is provided that includes a housing assembly, an element within the housing that has a longitudinal axis and defines therein at least one cell, a shape altering material housed within the at least one cell, and a source of activation energy operatively connected to the cell for activating the shape altering material to effect a change in the size of the at least one cell. The element may be operatively connectable to a driving member of an instrument such that the change in the size of the cell is translated to the driving member to facilitate the production of work.

In certain preferred embodiments, one or both of the shaft assembly and the actuator may be incorporated into a surgical instrument. In these embodiments, the surgical instrument may include an end effector, a shaft assembly operatively connected to the end effector, at least one cell defined within at least one of the shaft assembly or the end effector, a shape altering material housed within the at least one cell, and, an actuation assembly for selectively activating the shape altering material to effect a change in the at least one cell.

The shape altering material may be a wax, a polymeric phase change material, a conductive plastic, an expandable foam, or a magneto rheologic fluid.

The actuation assembly may include a source of activation energy, an activation control member positioned, for example, on a control portion operatively connected to the proximal end of the instrument for selectively applying the activation energy, and a link from the control member to the at least one cell for delivering the activation energy to the cell to activate the shape altering material.

The activation energy may be light, heat, electricity, magnetism, chemical energy (exothermic or endothermic), or pneumatic energy or hydraulic energy. The source of activation energy may be an external source linked to the activation control member, such as an electric outlet or a source of radiation within a desired rage of wavelengths, or an internal storage source for storing activation energy derived from an external source, such as a rechargeable battery, or a self-contained internal source, such as a replaceable battery or pressure sensor.

In certain embodiments, the shaft assembly may include an elongate shaft having a longitudinal axis and a plurality of cells formed in the shaft with each cell containing an amount of the shape altering material.

In certain embodiments, each of the plurality of cells may form a discrete pocket. The plurality of pockets may be arranged at intervals along the length of the shaft. In various embodiments, the shaft may be segmented and each pocket of the plurality of pockets is positioned between different adjacent segments along the axis of the shaft wherein selective activation of the shape altering material effects bending of the shaft in a predetermined direction. In other embodiments, the plurality of pockets may be positioned between different adjacent segments along opposing sides of the length of the shaft wherein selective activation of the shape altering material effects bending of the shaft in at least one of two predetermined directions. A further embodiment provides the plurality of pockets positioned between different adjacent segments along three equi-distant lengths of the shaft wherein selective activation of the shape altering material effects bending of the shaft in any predetermined direction through one or more 360° rotations, depending on the pitch and diameter of the shaft. The plurality of discrete pockets may also be formed into rings around the axis of the shaft.

In alternative embodiments, each of the plurality of cells may form a column along a portion of the length of the shaft. One or more channels may be formed in the shaft for carrying the activation link to the cells.

In other embodiments, the shaft assembly may include a plurality of concentric tubes. For example, there may be in various embodiments, a plurality of concentric tubes spaced such that an annular space is defined between adjacent concentric tubes. In various embodiments, there may be an inner tube, and at least one outer tube, and an annular space defined between the inner tube and the adjacent outer tube, wherein the inner tube defines a central lumen along its length. The shaft assembly may include a plurality of elongate flexible columns alternating with a plurality of elongate cells within the annular space. In another embodiment, the shaft assembly may include a plurality of annular solid segments alternating with a plurality of annular cells within the annular space. In another embodiment, the shaft assembly may include a first coil wound in a clockwise spiral positioned within the annular space. Alternatively, or in addition, there may be a second coil wound in a counterclockwise spiral within the annular space. In the embodiment having both the first and the second coil, the coils are positioned adjacent to each other within the annular space. The annular space in this and various embodiments may define the cell containing the shape altering material.

In certain embodiments of the surgical instrument the at least one cell may be in the end effector, in addition to or instead of, in the shaft assembly. In such embodiments, the end effector may include a housing, an element within the housing having a longitudinal axis and defining therein at least one cell, a plunger movable in an axial direction through the element, wherein the plunger includes a barrier plate for dividing the cell within the element into two chambers. In this embodiment, the shape altering material may be one of the expandable foam or the phase-change material and is housed within at least one of the two chambers. Activation of the shape altering material effects one of expansion or contraction of the shape altering material to move the plunger in one of a first or a second axial direction through the element.

In certain embodiments, each of the two chambers may contain a different shape altering material such that activation energy delivered to the two chambers effects expansion of the shape altering material in one chamber and contraction of the shape altering material in the other chamber to assist movement of the plunger in one of the first or the second axial direction. A spring may be provided within the element for biasing the plunger in a desired one of the first or the second axial direction.

The end effector may be any suitable known end effector, such as a cartridge for holding one or more tissue fasteners, such as staples or clips, wherein the plunger is positioned adjacent the tissue fastener, such that expansion of the shape altering material moves the plunger to eject a tissue fastener from the cartridge.

The end effector may, for example, be a pair of graspers having expandable jaws, such that expansion of the shape altering material moves the plunger to alter the jaws from one of an open or a closed configuration. For example, expansion may open one or both sides of the jaws and contraction of the shape altering material may move the plunger to close one or both sides of the jaws, or vice versa.

In certain embodiments, the end effector may include a cylinder defining a cylindrical space therein and having a central axial rod. The at least one cell may be formed within the cylindrical space between first and second end walls, a stationary radial wall attached to the rod, and a movable radial wall rotatably attached to the rod. When the shape altering material, for example, is a phase change material, activation effects a change of phase resulting in one of expansion or contraction of the phase change material thereby effecting rotation of the movable radial wall about the rod for the production of radial motion.

FIGURES

Various features of the embodiments described herein are set forth with particularity in the appended claims. The various embodiments, however, both as to organization and methods of operation, together with advantages thereof, may be understood in accordance with the following description taken in conjunction with the accompanying drawings as follows.

FIG. 2 is an embodiment of the surgical instrument of FIG. 1 wherein the shaft is in a rigidized mode, with a flexible configuration shown in chain line.

FIG. 3 A-A is a cross-sectional view of the shaft through the line A-A of FIG. 2.

FIG. 4 A-A is a cross-sectional view of an alternative embodiment of the shaft through the line A-A of FIG. 2.

Figure 5:
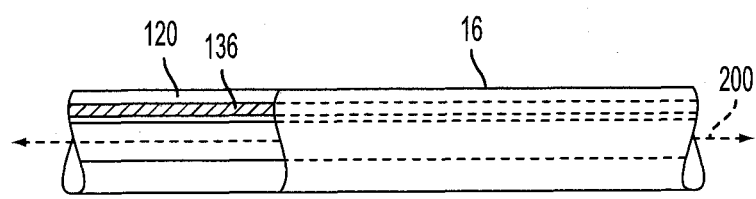

FIG. 5 is a view of a shaft having a cell in the form of at least one column.

Figure 6:
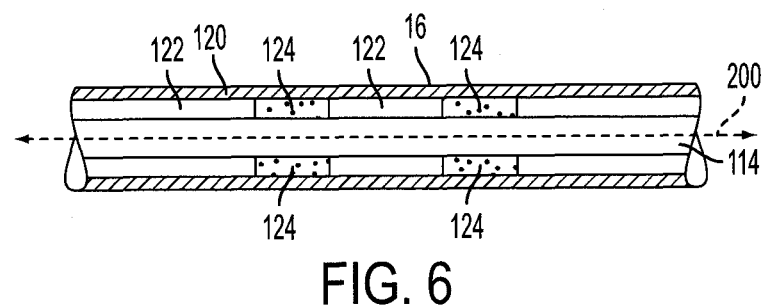

FIG. 6 is a view of a shaft having an alternative embodiment of cells alternating with solid sections of the shaft.

Figure 7:
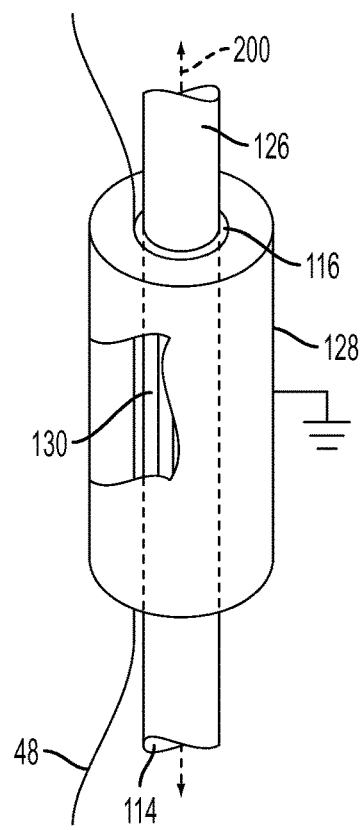

FIG. 7 is a partial sectional view of a shaft assembly having inner and outer tube layers with a shape altering material contained in between.

Figure 8:
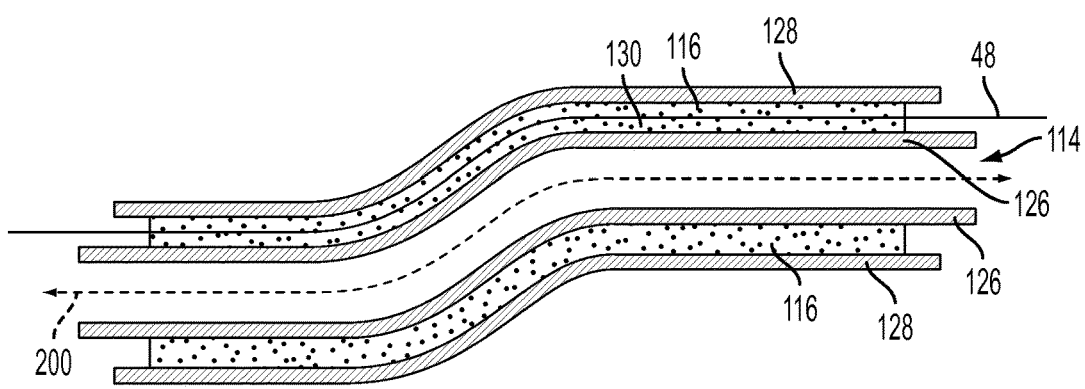

FIG. 8 is a side sectional view of the shaft configuration of FIG. 7 in a partially flexed or unrigidized mode.

Figure 9:
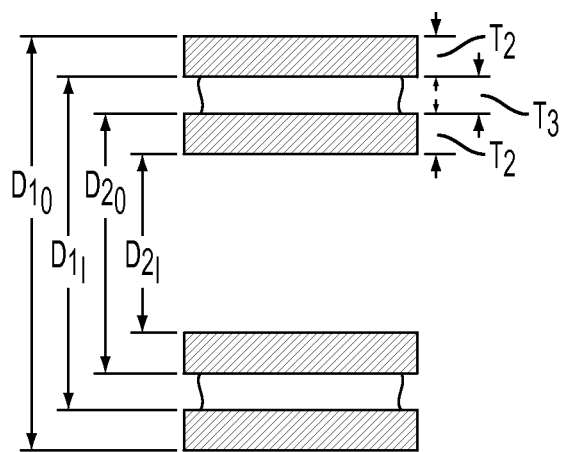

FIG. 9 is a partial side sectional view of an embodiment of a shaft assembly configuration having inner and outer tubes with a shape altering material contained in between.

Figure 10:
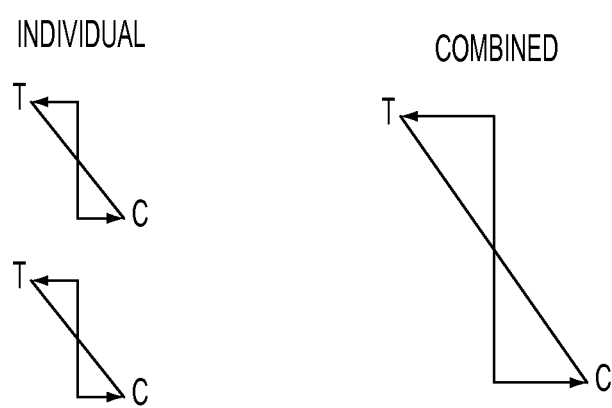

FIG. 10 is a view of the stress relationship for the individual and combined inner and outer tube members of a shaft assembly.

Figure 11:
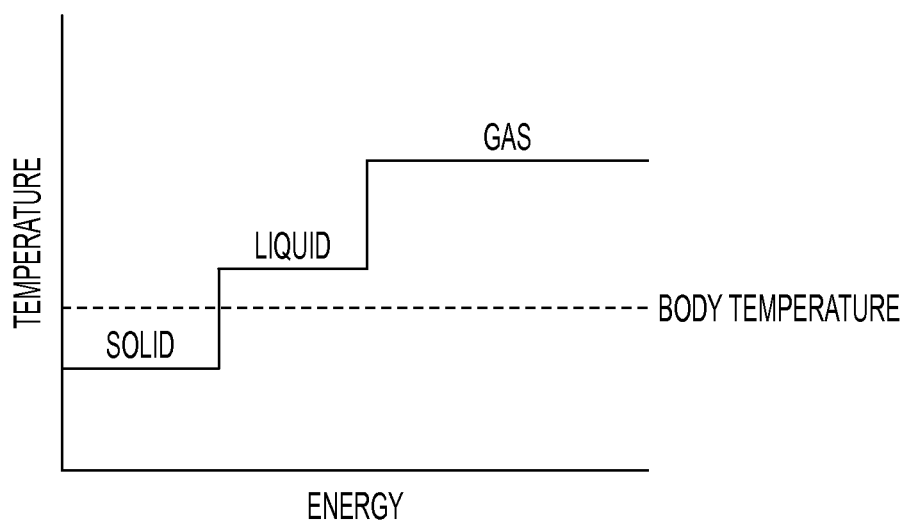

FIG. 11 is a curve showing the phase change characteristics of one embodiment of the shape altering material.

Figure 12:
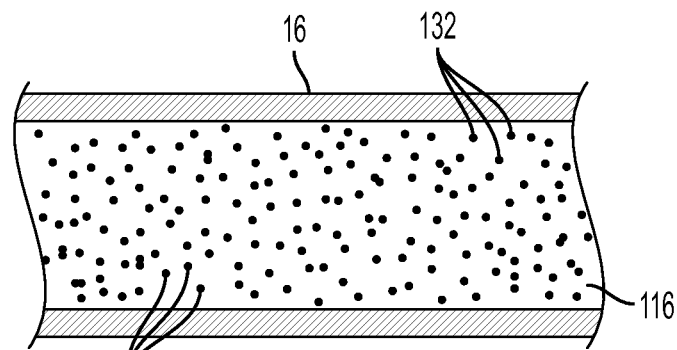

FIG. 12 is a view of a magneto rheological shape altering material in a flexible mode in a section of a cell.

Figure 13:
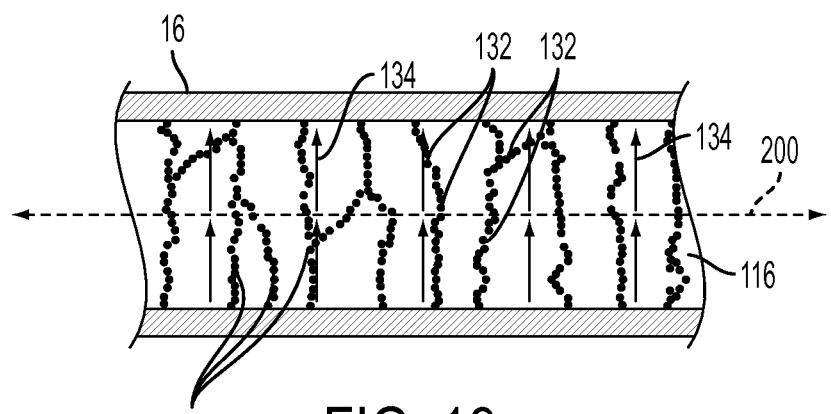

FIG. 13 is a view of the magneto rheological shape altering material of FIG. 12 in a rigidized mode.

FIGS. 14 A-E are side sectional and cross-sectional views of alternative embodiments of sets of cells having pockets at the junctions of a segmented shaft.

FIG. 15 is a view of an alternative embodiment of an actuation cell containing a shape altering material in both chambers that effects motion in either of two directions.

FIG. 16 is a cross-sectional view of an alternative embodiment of an actuation cell containing a shape altering material that effects rotational motion.

Figure 17:
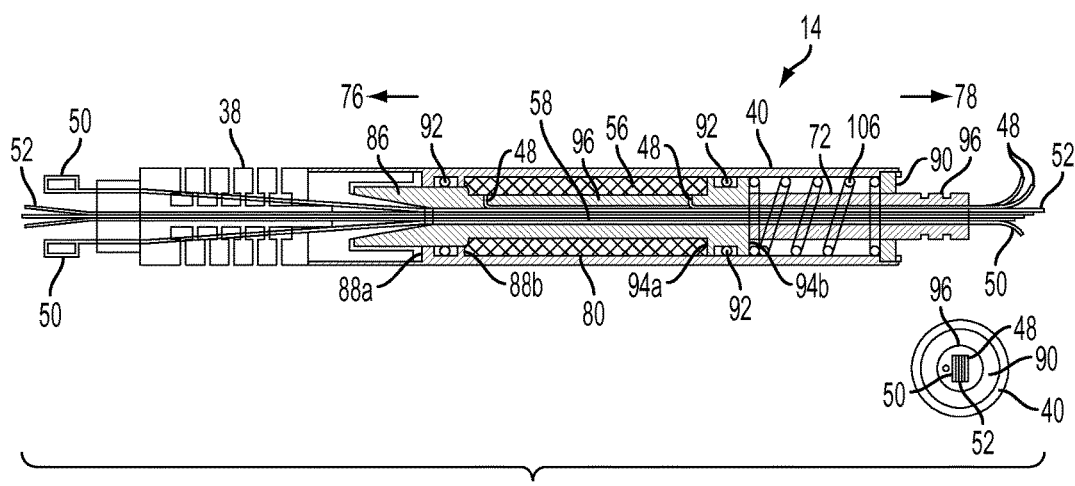

FIG. 17 is a side sectional view and end view of an embodiment of an end effector with an actuation cell.

Figure 18:
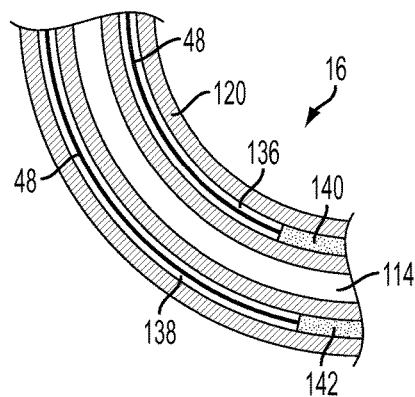
Figure 19A:
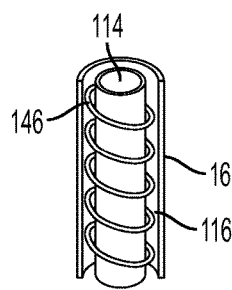
Figure 19B:
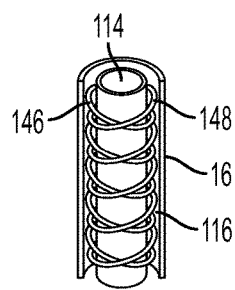
Figure 19C:
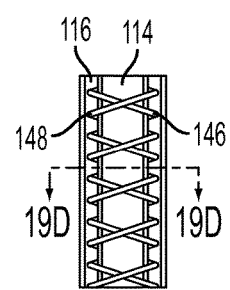
Figure 19D:
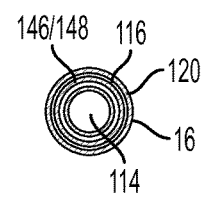

FIG. 18 is a side sectional view of a curved shaft having at least two columnar cells.

FIG. 19 A-D are sectional views of an alternative embodiment of a shaft having one or two coils that spiral around an annular cell in opposing directions.

Figure 20:
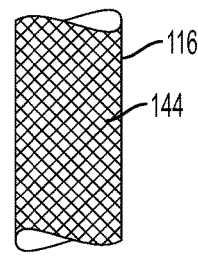

FIG. 20 is a partial view of a shaft having a woven coil configuration.

Figure 21:
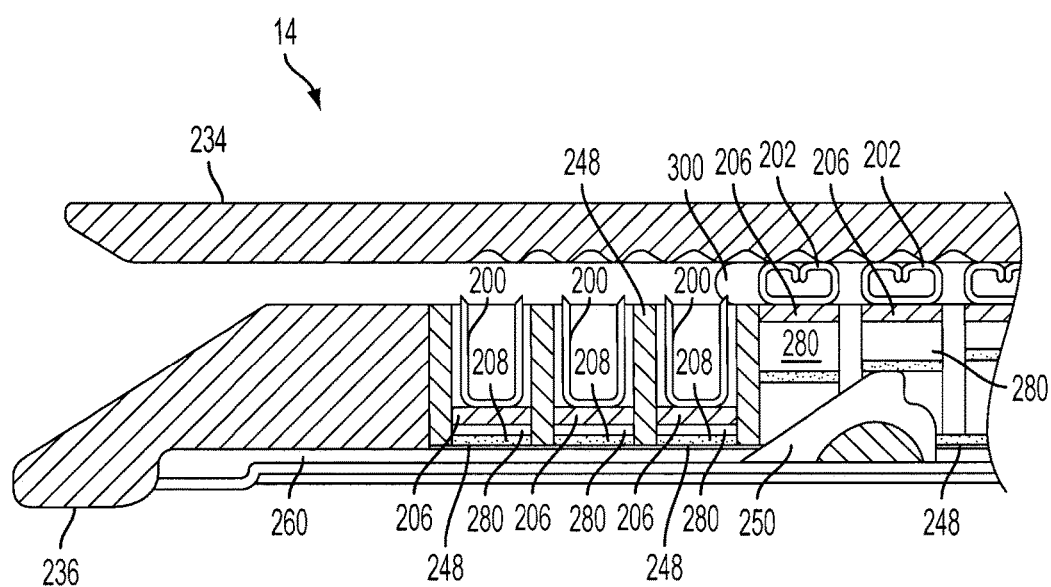

FIG. 21 is a section view of an embodiment of a surgical stapler on an end-effector of a surgical instrument showing the shape altering material in a contracted state in a cell under a stapler driver and unused staples in a stapler sled and in an expanded state in the cell under staples that have been pressed into tissue.

Corresponding reference characters indicate corresponding parts throughout the several views. The exemplifications set out herein illustrate various embodiments of the invention, in one form, and such exemplifications are not to be construed as limiting the scope of the invention in any manner.

DESCRIPTION

Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and do not necessarily limit the scope of the embodiments, the scope of which is defined solely by the appended claims.

Reference throughout the specification to "various embodiments," "some embodiments," "one embodiment," or "an embodiment", or the like, means that a particular feature, structure, or characteristic described in connection with the embodiment is included in at least one embodiment. Thus, appearances of the phrases "in various embodiments," "in some embodiments," "in one embodiment," or "in an embodiment", or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation.

It will be appreciated that the terms "proximal" and "distal" may be used throughout the specification with reference to a clinician manipulating one end of an instrument used to treat a patient. The term "proximal" refers to the portion of the instrument closest to the clinician and the term "distal" refers to the portion located furthest from the clinician. It will be further appreciated that for conciseness and clarity, spatial terms such as "vertical," "horizontal," "up," and "down" may be used herein with respect to the illustrated embodiments. However, surgical instruments may be used in many orientations and positions, and these terms are not intended to be limiting and absolute.

As used herein, the term "biocompatible" includes any material that is compatible with the living tissues and system(s) of a patient by not being substantially toxic or injurious and not causing immunological rejection. "Biocompatibility" includes the tendency of a material to be biocompatible.

Body temperature as used herein means core body temperature, which is generally about 98.6° F. (37.0° C.) measured orally, but can vary depending upon factors such as exercise, sleep, food or drink consumption, the time of day, or the age or health of the individual. Adult body temperatures below about 95° F. and above about 106° F. are dangerous to life and health. Children's body temperatures vary over a larger range. Those skilled in the art will recognize that "body temperature" is a range of temperatures around 98.6° F. (as measured orally), greater than 95° F. and less than 106° F.

As used herein, the term "longitudinal axis", with respect to an instrument, means the exact or approximate central axis defined by said instrument along its greater dimension, i.e., along its length, from its distal end to its proximal end, and vice versa, and is not intended to be limited to imply a straight line, wherein, for example, an instrument includes a bend angle or curves as described herein, it is intended that "longitudinal axis" as used herein follows such bend angle or curve. As used herein, the term "axial" or "axial movement" or variants thereof, with respect to an instrument or a component of an instrument, means the movement in the direction of the longitudinal axis of such instrument.

As used herein, the term "patient," used herein, refers to any human or animal on which a surgical procedure may be performed. As used herein, the term "internal site" of a patient means a lumen, body cavity or other location in a patient's body including, without limitation, sites accessible through natural orifices or through incisions.

As used herein, the term "operatively connected" with respect to two or more components, means that operation of, movement of, or some action of one component brings about, directly or indirectly, an operation, movement or reaction in the other component or components. Components that are operatively connected may be directly connected, may be indirectly connected to each other with one or more additional components interposed between the two, or may not be connected at all, but within a position such that the operation of, movement of or action of one component effects an operation, movement or reaction in the other component in a causal manner.

The use of shape altering materials to facilitate the desired functioning of various portions of instruments, such as surgical instruments, is described herein. The shape altering material may be a wax, a polymeric phase change material, a shape memory material, an expandable foam, a magneto rheologic fluid, or a Ferro fluid. Waxes and polymer formulations, for example, can respond to activation means such as temperature, light, electrical, chemical that cause a phase change and results in expansion of the material or rigidization to change the shape of a cell or other chamber in which the material is contained.

Figure 1:
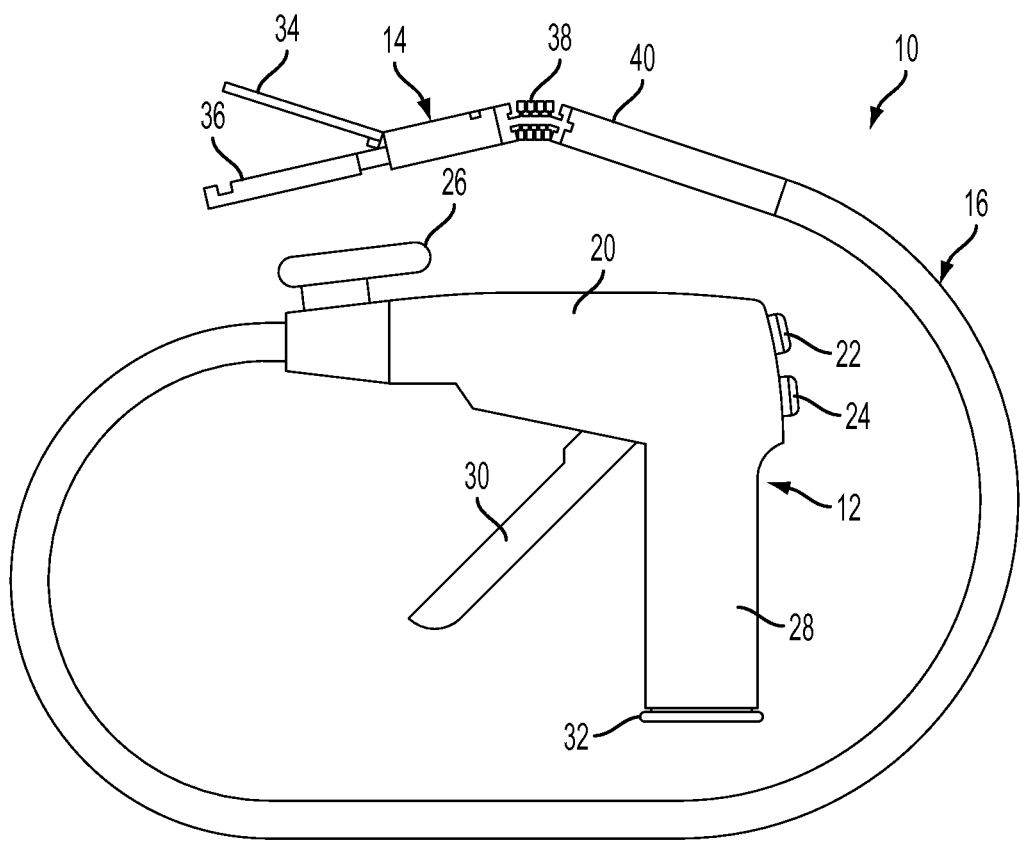
FIG. 1 is an embodiment of a surgical instrument having a shaft in a flexible mode and an end effector.

For ease of description, the various embodiments will be shown as used with a surgical instrument, such as that shown in FIG. 1. Those skilled in the art will appreciate, however, that the shaft assembly described herein may be used with any instrument in which it would be advantageous to selectively rigidize all or portions of an otherwise flexible shaft, or to unrigidize all or portions of an otherwise rigid shaft, or to change the rigidity of the shaft along portions thereof while in use to accommodate changing requirements, all from a control member remote from the portion of the shaft to be changed. Rigid, rigidity, or rigidize as used herein shall mean holding or maintaining a shape. Those skilled in the art will appreciate, however, that "rigid" and "unrigidize" and the like are relative terms. Rigidity, or lack thereof, is characterized by a load being distributed across the component, such as the shaft 16 described herein. Thus, rigidization by using the shape altering materials can create proportional control resulting in relatively stiffer but not necessarily completely rigid shafts having steel-like stiffness. Rigidization may also result in a completely rigid shaft 16. Rigid, rigidity, or rigidize and unrigidize or flexible, and similar terms as used herein shall include such relative increases and decreases, respectively, in stiffness and the ability to hold or maintain a shape.

Similarly, the actuator described herein for use with an end effector of a surgical instrument may be used to produce work in a similar manner in other working instruments. The two can be combined into one instrument allowing tissue access and subsequent end effector manipulation to gain tissue access for manipulation, diagnosis, or treatment.

In certain preferred embodiments, one or both of the shaft assembly and the actuator may be incorporated into a surgical instrument. In these embodiments, the surgical instrument may include a control portion, an end effector, a shaft assembly positioned between, and operatively connected to each of, the control portion and the end effector, at least one cell defined within at least one of the shaft assembly or the end effector, a shape altering material housed within the at least one cell, and, an actuation assembly for selectively activating the shape altering material to effect a change in the at least one cell. The various features may be integral in a single device, or may be separate but integrated for ease of replacement or interchangeability. For example, a single control member may be releasably attachable to a variety of different types of end effectors and each may be releasably attachable to a variety of different shaft assemblies.

Referring to FIG. 1, a surgical instrument 10 is shown having a control member 12, a shaft 16 and an end effector 14. Any suitable end effector 14 may be used, such as a grasper, retractor or dilator, or no end effector may be used when the function of the shaft, for example, is to provide a channel for delivery of other items to a site within a patient. The illustrative end effector 14 shown in FIG. 1 is a stapler having upper and lower clamp jaws 34, 36, a rotating joint 38 for adjusting the position of the jaws 34, 36, and a drive portion 40.

Control member 12 may include a control housing 20 and a hand piece 28 with a lever 30. The control member 12 may be used to direct the angle and degree of bend in the shaft 16 and to control the work of the end-effector 14. For example, the lever 30 may be squeezed to a desired degree to effect the change in rigidity of the shaft 16 or the operation of the end effector 14. Control knobs 22, 24 and a head control dial 26 are provided in addition to lever 30 for controlling various functions of the end effector 14 or shaft 16, such as, for example, opening and closing of the jaws 34, 36, rotating the rotating joint 38, forming and ejecting a staple, or clipping, cutting, and manipulating tissue, effecting the rigidity of the shaft 16, lighting an internal body cavity or lumen, and the like. A battery compartment 32 is provided to house a rechargeable or replaceable battery. Any standard battery for use with surgical or diagnostic instruments may be used.

FIG. 2 illustrates schematically a general embodiment of the internal electronics within the control member 12. An on-off switch 44 triggers the flow of activation energy, such as an electric current, through wires 48 through the shaft 16 (and in some embodiments, the cells 116 (e.g., FIGS. 3, 4, 7, 8 etc.), described in more detail below, positioned in the shaft) to the end effector 14. A light 42 may be provided to signal whether the power is on or off. A gauge 18 may be provided to show the level of power being delivered. A contact, such as ring contact 46 at head control dial 26 may be provided to further control the direction of the flow of activation energy to wires 48.

Those skilled in the art will recognize that other electronic configurations may be used and that other means of control may be used to deliver activation energy where needed in the instrument 10. The sources of activation energy may be provided by tethered means, such as electricity, in any appropriate voltage or current needed, delivered through a standard cable or wire plugged into a wall outlet or power strip to a heating element. A source of activation energy may also be provided by fluid in the form of pneumatic or hydraulic pressure, also delivered through a cable or tubing from a pressurizable source of gas (e.g., $CO_2$ or Argon) or liquid (e.g., pumped saline). Tubing connects to passages such as passages 118 shown in FIG. 4A-A, that egress through external holes. The media flow heats or cools the shaft, and may be the only temperature change agent or may be combined with other temperature change agents, for example, to cool a heat element. A source of activation energy may also be provided by light delivered in any wavelength suitable for use as activation signals. Fiber optics in passages with light reactive material may be turned on or off by turning off the light source or block the light path.

Activation energy may also be provided by untethered means, such as a built in or removable, replaceable battery, or a sensor, such as a piezo electric sensor, for generating signals in response to changes in pressure or motion. A handle may contain a component comprising a floating magnet within a coil (moves when handle is shaken) to create a flow of electrons that charges a capacitor for electrical dispensing i.e. to a heating coil. Untethered activation energy may also be provided by chemical energy generated, for example, from an exothermic or endothermic chemical reaction when two or more reactants, separated by suitable known means, are brought together. Passages 118 may contain reagents with a divider element that when removed, punctured, or otherwise breached, allows the reagent to mix and the reaction to take place. While reversible materials are commercially available and will be known to those skilled in the art, a one way reaction may be more practical in certain applications.

A base charged source of activation energy which stores energy from external source may also be provided in the form of a rechargeable battery, induction/capacitive coupling. For example, coils in a handle and base can be structured to act like a transformer allowing a current to flow and charge a capacitor for electrical dispensing i.e. to a heating coil. Another form of based charged source of activation energy may be provided by heat transfer, that is a heat or cold sink in the handle or shaft of the instrument is charged and moved to make or break contact with an element having phase change property.

The shaft 16 is shown in a curved mode in FIG. 1 and in both linear mode in FIG. 2. Phantom chain lines in FIG. 2 show an alternative configuration wherein portions of shaft 16 may be linear and portions curved to allow the shaft 16 to bend and curve where needed to accommodate the anatomical configuration of the patient at the site of a procedure or along the path to the site of a procedure. Curvature of the shaft 16 may be in a two or three dimensional orientation or both. While in the rigid mode, the shaft 16 of an instrument 10 holds its position to create a fixed linear, curved, or serpentine path as needed for mechanical controls or accommodating a patient's anatomical features. In the flexible mode, the shaft 16 can be manipulated to a desired shape without trauma to the tissue as well as allowing easier passage through a patient's body cavity or lumen if needed.

In various embodiments of shaft 16, cells 116 are provided that contain a shape altering material. In FIGS. 3 A-A and 4 A-A, alternative embodiments of a shaft configuration taken through the line A-A of FIG. 2 are shown. In FIG. 3 A-A, the shaft 16 has a central lumen 114 along the longitudinal axis 200 of shaft 16, and one cell 116 or one set of cells 116 along one side of shaft 16.

An actuation link 48, such as a wire for transmitting electrical or heat generating energy, a cable for delivering light at a desired wavelength, or a channel for delivering a pneumatic or hydraulic fluid, runs through cell 116 or set of cells 116 to deliver activation energy to each cell 116 to activate the shape altering material to effect a change in the material and thereby, a change in the rigidity of cell 116 or of one or more of the pockets 124 within the set of cells 116.

See, for example, FIG. 6. The type of activation energy required will depend on the type of shape altering material used.

The shape altering material may be activated by heating when, for example, the material is a phase change material or a wax. An example of heating the phase change material or wax includes winding the activation links 48, in the form of heating elements, such as wires, around the cell 116, with the wire entering at one end of the cell 116 and exiting at another end, and winding around the cell 116 in between the entry and exits, similar to the winding of a thread in a bobbin. In another example, activation links 48 may be wound around an independent structure instead of the cell 116, but operatively linked to the cells 116 to transfer the heat to the phase change material or wax. In another example, a conductive heat resistive matrix may be formed where conductive particles are dispersed throughout the phase change material in the cell 116 and heated by application of heat to the cell 116 to spread the heat throughout the phase change material. In another embodiment, the heating elements 48 may be in the form of a self supporting coil within the phase change material.

In FIG. 4 A-A, shaft 16 has a central lumen 114, two cells 116 or two sets of cells 116 on opposite sides of shaft 16, and two passages 118 for carrying the activation links 48 through the shaft 16. The activation links 48 in this embodiment may branch off at intervals to enter each cell 116 to activate the shape altering material. The passages 118 also allow for passage of activation links 48 for end-effector controls, such as: the mechanical operation of jaws, knives, and staples, as well as the delivery of energy in any suitable form, and any combination thereof. A multi-lumen shaft 16 for example, allows for both fluid delivery for pneumatic or hydraulic control, and other activation links 48, such as wires or sensors, as appropriate.

The central lumen 114 may also be used to deliver surgical tools or instruments, such as sutures, cameras, blades, and graspers, to a site of interest. In various embodiments, shaft 16 may not have a central or an off set lumen, but may be used to deliver an end effector 14 attached to the end of shaft 16. In such a solid embodiment, cells 116, with or without separate passages 118 for activation links 48 may define the only cavities or open spaces in the solid body 120 of shaft 16.

The cells 116 in shaft 16 can be configured in a variety of different ways. As shown in FIGS. 5 and 6, the cells 116 may be formed as one or more elongate columns 136 running along a portion of or all of the length of shaft 16 through the shaft body 120, or may form pockets 124 that alternate with solid segments 122 in the shaft body 120 along all or a portion of the length of shaft 16. The cell 116 or set of cells 116 may run in a direction parallel to or generally parallel to the longitudinal axis, or the cell 116 or set of cells 116 may run in a spiral around a portion of, or all of the length of shaft 16. The set of cells 116 may form a plurality of discrete pockets 124 running parallel or generally parallel to the longitudinal axis 200, or spiraling around a portion of, or all of the length of shaft 16.

In various embodiments having cells 116 in the form of two or more columns 136, 138 formed in the body 120 of shaft 16, as shown in FIG. 18, for example, each column may contain a different shape altering material 140 or 142 that may be activated to change the degree of rigidity under different conditions. For example, one column 136 may contain a phase change material 140 that changes phase from a solid to a liquid at a first temperature, such as a predetermined body temperature, and another column 138 may contain a phase change material 142 that changes phase at a second temperature, different from the first temperature, or may contain a different kind of shape altering material, such as, for example, a wax, or an expandable foam. An example of the bending behavior of such a shaft is shown in FIG. 18, wherein the two cells 116 in the form of columns 136, 138 on opposite sides of shaft 16 contain different shape altering materials 140, 142 that are activated to change the degree of rigidity at different rates, such that one side of shaft 16 increases or decreases its length relative to the other side resulting in a curved shaft. The direction and degree of the curve can be controlled by controlling the timing and degree of activation of the shape altering materials 140 and 142 in columns 136 and 138, respectively.

FIGS. 7 and 8 illustrate a shaft 16 assembly having inner and outer tubes 126 and 128, respectively, defining an annular space 130 between a combined length of the inner and outer tubes 126, 128. The annular space 130 between the tubes 126 and 128 can function as the cell 116 as shown in FIG. 7, or the cell 116 can form one or more elongate columns or discrete pockets that run along the length of annular space 130, similar to the configuration shown in FIGS. 5 and 6. One or more activation links 48 may run through the annular space 130. The inner and outer tubes 126, 128 may be movable longitudinally relative to each other while the shape altering material in cell 116 is in the flexible mode, but may be constrained against relative movement when the shape altering material is in the rigidized mode.

Referring to FIGS. 9 and 10, the dual tube shaft assembly offers advantages in increased moment of inertia. Referring to FIG. 9, $D_1$ is the outer tube 126 and $D_2$ is the inner tube 128, $D_{1O}$ is the outer diameter of the outer tube 126, $D_{1I}$ is the inner diameter of the outer tube 126, $D_{2O}$ is the outer diameter of the inner tube 128 and $D_{2I}$ is the inner diameter of the inner tube 128. The thickness of outer and inner tubes 126, 128 is represented by $T_1$ and $T_2$. The thickness of the central lumen is represented as $T_3$.

The combination of two tubes 126, 128 and a shape altering material creates a stiffer shaft assembly 16 than the individual tubes alone. Classic stress diagrams are shown in FIG. 10 for each tube 126, 128. In FIG. 10, T=tension and C=compression. A shape altering material, such as a phase change material in the liquid state, creates a shaft with the stiffness equal to the sum of their respective physical and dimensional properties. The shape altering materials in the solid state bond the two tubes 126, 128 together creating a stiffer structure (i.e., a structure having an increased moment of inertia) which will hold the tubes 126, 128 in their relative positions at the time of rigidization, e.g., straight, curved, or any desired shape.

$$\text{Moment of Inertia, } I = \frac{\pi(D_O^4 - D_I^4)}{64},$$

where $D_O$ is outside diameter, $D_I$ is inside diameter of either the inner or the outer tube 126, 128. When acting as a solid wall when the shape altering material bonds the tubes together, the moment of inertia of the combined tubes forming the shaft assembly is greater than the sum of the moments of inertia of each tube alone.

$$I = \frac{\pi(D_{1O}^4 - D_{2I}^4)}{64} > I_{tube\ 1} + I_{tube\ 2},$$

where $D_{1O}$ is the outer diameter of the outer tube 126 and $D_{2I}$ is the inner diameter of the inner tube 128. As the moment of inertia increases, there will be less deflection of the tubes 126, 128.

An alternative means of control can be achieved by varying the tubing wall thickness, T, to create a wide range of shaft stiffnesses. For example, concentric 0.062 inches thick thermo plastic rubber, such as Kynar™, or any medically approved tubing, may be used. These materials are commercially available in a variety of durometers. Tubes with a thin 0.005 inch layer of shape altering material, such as tetracosane, will hold the shape of shaft 16 but change the stiffness of the shaft assembly very little, whereas a 0.005 inch thick pvc wall and shape altering material having a 0.040 inch thick wall will result in a very flexible shaft when the shape altering material is liquid and a rigid shaft when the shape altering material is solid. Other suitable thermoplastic elastomeric materials are commercially available and include styrenic block copolymers, polyolefin blends, elastomeric alloys (TPE-v or TPV), thermoplastic polyurethanes, thermoplastic copolyester and thermoplastic polyamides. Examples of thermoplastic elastomeric materials products that come from block copolymers are STYROFLEX™ (BASF), KRATON™ (Shell chemicals), PELLETHANE™, ENGAGE™ (Dow Chemical), PEBAX™ (Arkema), ARNITEL™ (DSM), and HYTREL™ (E.I. Du Pont de Nemours). Commercially available elastomer alloys include: DRYFLEX™, MEDIPRENE™, SANTOPRENE™, GEOLAST™ (Monsanto), SARLINK™ (DSM), FORPRENE™, ALCRYN™ (E.I. Du Pont de Nemours) and EVOPRENE™ (AlphaGary).

When the phase change material bonds to tubing wall, the material becomes the shear member and the tubing becomes the stress member. The tubes can be treated to increase the adhesion of the phase change material. Treatment methods include, for example, cleaning, etching, or exposing the tubing to a corona arc.

Tubing material that is thin and has a higher heat transfer capacity on the exterior of the tubing is better suited for external temperature sources. In addition, or in the alternative, the tubing walls may contain fillers to change their properties. For example, the tubing walls may contain carbon fibers to increase thermal transfer properties.

The shape altering material may be a phase change material that changes phase from gas to liquid to solid at a temperature specific to the particular material. FIG. 11, for example, shows a graph of a phase change material that is solid at room temperature and less but changes from a solid to a liquid at or near a predetermined body temperature (e.g., about 97°-99° F.). Other phase change materials may be a liquid or a gas at room temperature and change phase to a solid or liquid, respectively, at a temperature below room or body temperature.

A phase change with its corresponding volume change occurs when the phase change materials reach the temperature at which they change phase (e.g. melting point). At that temperature, the material absorbs large amounts of heat without changing its temperature. When the ambient temperature in the space around the phase change material drops, the phase change material solidifies, releasing its stored latent heat. Phase change materials absorb and emit heat while maintaining a nearly constant temperature. A constrained volume can create high forces.

Tissue or body temperature acts as heat sink. As previously described, the phase change temperature can be above or below body temperature depending on use of the body as a heat source or heat sink. A heating element may also be used to hold the phase change material just above or below its transition temperature to make a faster phase change trigger.

Using available phase change diagrams, the phase change transition temperature can be used to control the shape altering characteristics from a rigidized to an unrigidized or flexed mode back to a rigidized mode or vice versa, as desired.

If the phase change material body is in the liquid phase at body temperature, then the device will be flexible. Cooling the phase change material will make it solid and stiffen the shaft 16. The patient's body temperature will change the phase change material back to liquid and the shaft 16 will regain flexibility.

If the phase change material body is in the solid phase at the predetermined body temperature, the shaft 16 will be rigid. Heating the phase change material to the appropriate temperature above the body temperature will change the phase to liquid and create a flexible condition in the cells 116 and thereby in the portion of shaft 16 where the cells 116 are positioned. Exposure of the phase change material again to the predetermined body temperature will hasten the return to the solid and rigid state. If, however, the transition temperature includes the body temperature, the energy needed to create the phase change is less and opens the kinds of activation sources available.

To cause a phase change material to alter states, energy to heat or cool the material is needed. Brittle phase change materials will fracture if overstressed, potentially limiting tissue contact pressure damage, but will re-crystallize and regain its rigid structure after being re-melted. Phase change materials with crystalline properties, such as tetracosane, are stiffer than polymers like paraffin. High purity phase change materials have greater stiffness than impure or blended materials.

Exemplary phase change materials include water.

Exemplary shape memory materials include metals, for example, NITENOL™ and plastics VERIFLES™ (styrene) manufactured by Cornerstone Research Group.

Exemplary waxes include Paraffin and tetracosane.

Exemplary expandable foams are commercially available from Cornerstone Research Group.

The shape altering material may alternatively be a magneto rheological material. Referring to FIGS. 12 and 13, a carrier oil with magnetic particles 132 dispersed throughout may be contained in the cells 116. Upon activation, the magnetic particles 132 line up and form chains along magnetic flux lines 134. The magneto rheological material may be used in the embodiment of cells 116 shown in FIGS. 5 and 6, for example, wherein the magneto rheological material would be contained in the columnar cell 136 shown in FIG. 5 or in the pockets 124 shown in FIG. 6.

Magneto rheological materials are fluids that contain micrometer sized magnetic particles (in the range of about 0.1 to 10 μm) in a carrier fluid, such as an oil, usually mixed with a surfactant. Surfactants in the carrier fluid reduce the rate and degree to which the magnetic particles 132 come out of suspension in the carrier fluid. When there is no applied magnetic field, the magnetic particles are in suspension and randomly distributed in the carrier fluid. In this mode, the shaft 16 will be flexible. When subjected to a magnetic field, the fluid increases its viscosity to become a viscoelastic solid and the magnetic particles align in chains along lines of magnetic flux perpendicular to the longitudinal axis of the cell 116, which, in most cases, is parallel to the longitudinal axis 200 of the shaft 16. When the fluid is contained between two poles, the chain of particles restricts movement of the fluid along the longitudinal axis of the cell 116. The restriction on movement of the fluid effectively increases its viscosity, rigidizing the cell 116 and the portion of shaft 16 in which the cell 116 is positioned. Any of the commercially available magneto rheological materials may be used as the shape altering material in cells 116. An alternate material is a Ferro fluid with smaller particles which will provide a more dense suspension.

The shaft is flexible when introduced at some entry point of a patient's body. A magnet can be positioned and turned on and off to give momentary stiffening of the shaft 16 for maneuvering. The flexible state allows the shaft to take shape, when, for example, a vaginal entry device needs to drape over the sacral prominence without applying pressure to compress tissue and nerves. The magnet may be external, internal or built into the shaft. A magnet built into the shaft could allow an external controller to control any or all segments of the shaft subject to magnetic zones created by loops of wire to create a magnetic field.

For example, to apply a magnetic field to activate the magneto rheological material when used in cells 116, an external magnet may be used, such as the type of external magnetic control device used in magnetic anchoring and guidance systems (MAGS). MAGS, which have been developed for use in minimally invasive procedures, generally include an internal device attached in some manner to a surgical instrument, laparoscope or other camera or viewing device, and an external hand held device for controlling the movement of the internal device. Each of the external and internal devices has magnets which are magnetically coupled to each other across, for example, a patient's abdominal wall. The external device of such a system and its associated magnets may be used to apply the magnetic field to the magneto rheological material in the cells 116. An internal magnet to establish a localized magnetic field. The strength of the magnetic field may be adjusted by adjusting the height of the external magnet or alternatively, the field intensity if using an electromagnet.

In various embodiments, shown in FIGS. 14 A-E, the shaft 16 may be segmented. In a similar manner, the rotating joint 38 of the end-effector 14 is shown as segmented. Although described with specific reference to the shaft 16, the following description of segmented sections applies to both the shaft and a bendable or twistable section of the end-effector 14, such as but not limited to the rotating joint 38 shown in FIGS. 1 and 2. One or more shaft 16 segments 102 will have a means, such as a flexible membrane lining for the segmented shaft, to allow separation at the junctions 110 between shaft segments 102 while maintaining a closed shaft. Separation of the edges at the junctions of adjacent segments 102 at one point will cause the adjacent segments 102 to angulate on one side creating a curved section of shaft 16. Controlling multiple segments 102 individually or in some combination will enable controlling the length and degree of curve. In certain embodiments, each of the plurality of cells 116 may form a discrete pocket 124 arranged at intervals along the length of the shaft 16, with each pocket 124 being positioned at the junction 110 between a different adjacent segment 102 along the longitudinal axis 200 of a solid (i.e., without a central lumen) shaft 16. See FIG. 14 A. Selective activation of the shape altering material in one or more of the pockets 124 effects bending of the shaft 16 in a predetermined direction along a desired portion of the shaft 16.

In other embodiments, as shown in FIG. 14 B, side to side motion of a shaft 16 can be provided by having two sets of cells 116 arranged along opposing sides of the length of the shaft 16 such that there are two pockets 124 positioned on opposite sides (e.g., at about 180° from each other) of the junction 110 between adjacent segments 102 of shaft 16. Selective activation of the shape altering material in this embodiment effects bending of the shaft 16 in at least one of two predetermined directions along a desired portion of the shaft 16.

A further embodiment shown in FIG. 14 C provides three sets of cells 116 arranged equi-distant from each other (e.g., at about 120° from each other) such that there are three pockets 124 positioned equi-distant from each other around the circumference of the juncture 110 of adjacent segments 102 of shaft 16. Selective activation of the shape altering material in this embodiment effects bending or twisting of the shaft 16 in any predetermined direction within 360°. In each of the foregoing embodiments, the pockets 124 may be positioned at either regular or irregular intervals of segments 102 along all or a portion of the length of the shaft 16. By way of example, a pair of pockets 124 in the embodiment having two sets of cells 116 may be positioned regularly at every junction 110 between adjacent segments 102 or at the junctions 110 between every second, third or fourth shaft segment 102. Alternatively, there may be pairs of pockets 124 (or one, three or more pockets) at every junction 110 of adjacent segments 102 for several segments in a row, followed several unpocketed segments, followed by pairs of pockets 124 or single columns of pockets 124 at every other junction 110 of shaft segments 102, or in any desired pattern suitable for the intended use of the instrument and shaft.

Segmented shafts allow for flexibility. An alternative to the segmented shaft with a flexible inner lining is a ball and socket design which enables a load to create increased friction to hold the shape. A cable may run through the center of the ball and socket arrangement. Referring to FIG. 14 A, a central activation link 48 when expanded by the shape altering material, such as a phase change material, pneumatic or hydraulic fluid, or chemical means, creates the friction needed to lock the segments 102 in place. Having two or more off-center lines that are simultaneously expanded like those shown in FIG. 14 B or C, will provide an alternate shape holding configuration. Multiple lines allow higher forces to be created or allow a smaller expansion member to maintain a lower force.

An alternate form shown in FIG. 14 D that can be used to either curve or tighten an assembly is a ring (continuous or segmented) with one, two or three activation links 48 that, depending on how they are activated, enables a curved or linear response. The plurality of discrete pockets 124 may be formed into rings positioned around the longitudinal axis 200 of the shaft 16, for example, at the juncture 110 of adjacent shaft segments 102, or where the shaft 16 is not segmented, at either regular or irregular intervals along all or a portion of the length of the shaft 16.

FIG. 14 E shows an embodiment of a series of pockets 124 in four sets of cells 116. In this embodiment, there may be a split shaft 16 or the sets of cells 116 may be used in, for example, the jaws of a grasper or another type of an end effector 14 having facing sections that would benefit from changing between a flexible and a rigid shape. Two sets of cells 116, arranged in off-set rows of pockets 124, are placed in each half shaft 16 or end effector 14 section.

The segmented motion can be achieved by the expansion of shape memory plastics or phase change materials such as wax. Use of more conventional power means such as reversible chemical reaction, pneumatic or hydraulic fluids may be used as well. To give a faster return after diminishing the elongation source, a wire 48 with springs applies a return to the shortened (straight) position.

In an alternative embodiment of shaft 16 and cells 116, coiled tubes may be used. Coils are flexible and can perform well in compression. Expansion of coils, however, will make the shaft 16 poor in tension. FIG. 19 shows a shaft 16 construction having a continuous annular cell 116 and oppositely wound coils 146 and 148 housed therein. One coil 146 is wound in a clockwise direction and the other coil 148 is wound in a counterclockwise direction. Either one of the two coils may be wound inside the other of the two coils. The dual coil construction, particularly when combined with a shape altering material, prevents the shaft from being crushed. A shape altering material, such as a phase change material, is placed in the annular cell 116 in between the coils 146 and 148, thus enabling the coils 146, 148 to become one stronger structure that can then be used to perform with greater tension and compression. By varying the coil material, wire size, mandrel diameter, and pitch, a large range of flexible properties, limited only by the available volume, can be created.

Referring to FIG. 20, an alternative configuration for the shaft 16 and cell 116 provides a woven wire pattern 144 in the annular cell 116 that has some give before engagement in tension, compression and torque. Integration with a shape altering material, such as a phase change material, can make the shaft 16 behave like a solid shaft and eliminate twisting of the shaft 16.

Various embodiments of the cells in their capacity as an actuator assembly may include one or more linear pushing and/or pulling cells 80 that may be used as an alternative to the mechanical drive system used for example in surgical stapler systems. A volume change in the cell 80 may be channeled to a smaller diameter section to increase the linear travel of a plunger 86, as described below. The volume of the actuator cell 80 or set of cells 80 and the activation energy input to each cell may be varied to accommodate a variety of end effectors 14 of any size or length of actuation.

FIG. 15 illustrates an example of a cell 116 used as an actuation cell 80 for the production of work by enabling pushing, pulling, or a reciprocating pushing and pulling motion. Actuation cell 80 is defined between a first end wall 88 and a second end wall 90. An axially movable plunger 86 having a mid plate 94 and a rod 96 is positioned in actuation cell 80, dividing cell 80 into a first chamber 82 and a second chamber 84. In the embodiment shown in FIG. 15, both chambers 82 and 84 contain a shape altering material. In other embodiments of the actuation cell 80, only one of the chambers 82 or 84 may contain a shape altering material. Seals 92 prevent leakage of the shape altering material from one chamber into the adjacent chamber. An activation link 48 as described previously is operatively connected to the cell 80 to activate a change in the shape altering material.

In the embodiment wherein both chambers 82, 84 contain shape altering materials, each chamber may contain a shape altering material different from the material in the adjacent chamber. As described above, the adjacent chambers 82, 84 may contain two different phase change materials, or two different expandable foams that are activated at different temperatures, or may contain two different kinds of shape altering materials that are activated under different conditions, or may contain the same or different shape altering materials with separate activation links to each chamber 82, 84 to effect a change in the state of the material at different times or to effect different changes in the state of the material at the same time.

When the shape altering material in chamber 82 is activated to cause the material to expand, the expanding material pushes mid plate 94 of plunger 86 in direction 78 (to the right in FIG. 15). The shape altering material in chamber 84 must be able to be compressed or must not fill the entire chamber. Pushing plate 94 pushes rod 96 in direction 78. When used in an end effector 14, rod 96 will be operatively connected to a component, such as a gear, a ramp, a movable platform, a pivot point, or the like, that performs or causes to be performed some work. Pushing rod 96 will apply force to the component to trigger the desired performance.

Similarly, when the shape altering material in chamber 84 is activated to cause the material to expand, the expanding material pulls mid plate 94 of plunger 86 in direction 76 (to the left in FIG. 15). The shape altering material in chamber 82 must be able to be compressed or must not fill the entire chamber. Pulling plate 94 pulls rod 96 in direction 76. The component in the end effector 14 to which rod 96 is operatively connected may be pulled back, to end the performance of the work or may be pulled back to rest the component for the next application of force sufficient to trigger the performance of work.

In certain embodiments, a spring 106 as shown in FIG. 17, can be incorporated adjacent to an end wall 88 or 90 of the actuation cell 80, or in one of the chambers 82 or 84 when only one chamber 82 or 84 contains the shape altering material. The spring 106 may be used to bias the plunger 86 toward the position in which the shape altering material in the adjacent chamber is in an unexpanded mode. The spring 106 may return the plunger 86 in a one way motion or return it to a neutral position in an actuation cell 80 configured for two way motion, like the cell 80 shown in FIG. 15. Spring 106 may be of any type of biasing member, such as a tension spring, a compression spring, a rotational spring, a leaf spring, or bellview washer.

FIG. 16 illustrates the cross sectional view of an embodiment of an actuation cell 80 that enables the production of work in a circular configuration for rotational applications. Examples of rotational motion are in plane axial rotation, a cam, or a screw. The degree of rotation may be any fractional or greater turn. In this embodiment of actuation cell 80, the plunger 86 includes a central rod 96, a fixed radial wall 98 and a movable radial wall 94. The shape altering material is contained in the cell 80 between the fixed and movable radial walls 98, 94. An activation link 48 as described previously is operatively connected to the cell 80 to activate a change in the shape altering material.

Activation of the shape altering material may expand the material forcing the rotational movement of movable radial wall 94 in a counterclockwise direction, as shown by the arrow in FIG. 16. Activation of the shape altering material may alternatively cause the shape altering material to contract. Movable radial wall 94 may be biased in the clockwise direction back into the contracted position by a spring or other biasing member, as described above, or by activation of a second shape altering material in the manner described with regard to FIG. 15. Those skilled in the art will recognize that, depending on the location of the shape altering material within cell 80 relative to fixed and movable radial wall 98, 94, the expansion and contraction of the shape altering material may cause rotation of the movable wall in a clockwise or counterclockwise direction, respectively. Those skilled in the art will appreciate that the movable radial wall 94 does not have to be in the center of the cell 80 and further, that the cell 80 may be partitioned to have one, two or more divisions, or chambers in the cells 80 in cross section.

The degree of axial, linear or rotational motion may be controlled by segmented heating elements or proportional resistance, with for example, a potentiometer or a rheostat, or by way of dynamic computer control. In this embodiment, the control member 12 may be operatively connected to an external computer, or may incorporate computer chips controllable with the various controls on control member 12, as described above.

Surface temperatures below 140° F. are not known to harm tissue, but temperatures at or above that temperature may. Therefore, when the speed and action of the plunger 86 is triggered by a thermal response, insulation of the area surrounding the actuation cell 80 is provided to avoid harm to tissue. Similarly, insulation may be provided around portions of shaft 16 if such high temperatures are used to trigger changes in rigidity.

An example of the type of work that may be triggered by the activation of the shape altering material in an actuation cell 80 is a surgical stapler. Referring to FIG. 17, an end effector 14 in the form of a surgical stapler with a jaw drive is shown. The end effector 14 shown includes a drive portion 40 and a rotating joint 38 from which extend rotating jaws 50 and ribbon drives 52 for stapling and cutting operations. Drive portion 40 that houses an actuation cell 80 which is divided into first and second chambers 56 and 72, respectively, by leading end walls 88a and 88b and mid plates 94a and 94b of plunger 86. First chamber 56 contains a shape altering material and second chamber 72 contains a spring 106 for biasing the mid plate 94 a, b of plunger 86 distally, in direction 76. The mechanical spring 106 maintains the rotating jaws 50 in a normally open position, when the activation energy is not applied. Seals 92, such as O-rings, are positioned in the space between each of the adjacent wall 88 a, b and plate sections 94 a, b. Plunger 86 includes a center rod 96 that extends from the leading end wall 88 through mid plate walls 90 through end wall 90 into a shaft 16 of an instrument 10 (not shown in this view. See FIGS. 1 and 2). Rod 96 includes a channel 58 along the longitudinal axis of rod 96 through which run the activation links 48 and ribbon drives 52 for stapling and cutting. Two activation links 48 branch off into actuation cell 80. The remaining activation links 48 continue forward, distally to the rotating jaw drives 50 and ribbon drives 52.

Activation of the shape altering material in the manner described in any of the embodiments described herein causes the material to expand, exerting force on the mid plate 94 a of plunger 86, thereby pulling the plunger 86 and its narrow channel 58 in the proximal direction (direction 78 in FIG. 17) allowing rotating drives 50 to expand outwardly, away from each other in a more open position. When the activation energy is discontinued or changed such that the shape altering material contracts, spring 106 pushes mid plate sections 94 a, b forward in the distal direction (direction 76 in FIG. 17) to squeeze rotating drives 50 into channel 58 forcing the drives 50 inwardly, towards each other in a more closed position. The actuation cell 80 in the embodiment of FIG. 17 can be configured such that the rotating jaws will be normally closed and powered to open.

The actuation cells 80 described herein can easily be adapted to numerous end effectors 14. For example, referring to FIGS. 1 and 2, the jaws 34, 36 can be configured to be normally closed and powered to open, or normally open and powered to close. The jaws 34, 36 may be configured to open in a non-symmetrical fashion. One jaw arm 34 or 36 may be fixed and the other movable.

The drive portion 40 and shaft 16 may be configured in any diameter with the limitation being that deliverable forces will be less with smaller diameters. A practical size range is from 2 mm to 12 mm diameters. Other dimensions may be used depending on the application.

In another embodiment, staple drivers 206 may sit on a platform or stapler sled 260 positioned in the bottom portion 236 of the end effector 14, above an actuation cell 280. End-effectors that comprise staplers and stapler drives are shown in U.S. Pat. No. 7,794,475, which is incorporated herein by reference. Instead of the driving mechanism shown in the prior art stapler systems, a shape altering material in an actuation cell 280 may be provided, which, when heated by a heating element 208 which may be connected directly or indirectly to an activation energy source 248, changes phase from solid to liquid, or more generally, changes from a contracted to an expanded state. The change to the expanded state changes the volume of cell 280, which applies force to the staple drivers 206 and ejects the staple 200 into tissue 300. The top portion 234 of the end effector 14 presses the staple into a closed position, designated by staples 202, as illustrated in the FIG. 21. In another embodiment, a knife (not shown) may be incorporated as part of the platform of the stapler sled that is raised when the shape altering material expands. The knife may be part of the same driver as the staple or may be independently raised with its own driver, activation source, and control. Surgical staples and knives of this kind are commercially available and well known in the art, so will not be described in detail herein.

When the shape altering material is an expandable foam, when heated, the foam can expand to forty times its volume to drive staple formation. The activation energy source may be any of the means identified herein. The expandable foam material may be any suitable known foam, such as the foam product available from Cornerstone Research Group, Inc; of Dayton, Ohio. One property of an expandable foam is a time delay from activation to expansion. This delay can be adjusted from seconds to minutes. Staplers are typically clamped on tissue 300 for a minute before firing the staples 200. As such, the foam may be selected and its activation controlled to provide a built in delay mechanism.

Those skilled in the art will appreciate that other configurations of foam expansion for pushing staples and cutting tissue directly or indirectly may be provided within the scope of the subject matter described and claimed herein.

In an alternative embodiment, a tapered wedge, similar to ramp 250 in FIG. 21, and a driver with wings may be provided. The wings (one side or two) have volume expansion causing a movement along the stapler sled's 260 long axle thereby moving the driver up the ramp (inclined plane) to drive the staple 200 out of the sled 260. This is a linear expansion that drives a sled 260 that sequentially fires staples 200 and cuts tissue 300. In yet another embodiment, a rotational cell, such as the cell shown in FIG. 16, may be used to raise the staple driver and knife.

Variations of the concept allow for multiple configurations wherein a number of extruded holes may be provided to accommodate cells of the phase change material and activation means. An offset activation may be used to allow a slower reaction time thereby gradually increasing or decreasing the degree of rigidity over time.

Although the Figures and description herein primarily reference shaft and cell components as being circular in cross section, those skilled in the art will recognize that other configurations may be used. For example, the shaft and cells or one of them, may form, in cross section, an oval, a square, a rectangle, a triangle or another polygonal shape, or an irregular shape. Conforming changes in configuration would be made in any appropriate end walls, movable walls, plungers and plunger mid plates of the cells 116 or 80.

Except as otherwise noted, the articles "a", "an", and "the" mean "one or more".

Except as otherwise noted, all amounts including quantities, percentages, portions, and proportions, are understood to be modified by the word "about", and amounts are not intended to indicate significant digits.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

The embodiments of the devices described herein may be introduced inside a patient using minimally invasive or open surgical techniques. In some instances it may be advantageous to introduce the devices inside the patient using a combination of minimally invasive and open surgical techniques. Minimally invasive techniques may provide more accurate and effective access to the treatment region for diagnostic and treatment procedures. To reach internal treatment regions within the patient, the devices described herein may be inserted through natural openings of the body such as the mouth, anus, and/or vagina, for example. Minimally invasive procedures performed by the introduction of various medical devices into the patient through a natural opening of the patient are known in the art as NOTES™ procedures. Some portions of the devices may be introduced to the tissue treatment region percutaneously or through small-keyhole-incisions.

Endoscopic minimally invasive surgical and diagnostic medical procedures are used to evaluate and treat internal organs by inserting a small tube into the body. The endoscope may have a rigid or a flexible tube. A flexible endoscope may be introduced either through a natural body opening (e.g., mouth, anus, and/or vagina) or via a trocar through a relatively small-keyhole-incision incisions (usually 0.5-2.5 cm). The endoscope can be used to observe surface conditions of internal organs, including abnormal or diseased tissue such as lesions and other surface conditions and capture images for visual inspection and photography. The endoscope may be adapted and configured with working channels for introducing medical instruments to the treatment region for taking biopsies, retrieving foreign objects, and/or performing surgical procedures.

Preferably, the various embodiments of the devices described herein will be processed before surgery. First, a new or used instrument is obtained and if necessary cleaned. The instrument can then be sterilized. In one sterilization technique, the instrument is placed in a closed and sealed container, such as a plastic or TYVEK® bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility. Other sterilization techniques can be done by any number of ways known to those skilled in the art including beta or gamma radiation, ethylene oxide, and/or steam.

Although the various embodiments of the devices have been described herein in connection with certain disclosed embodiments, many modifications and variations to those embodiments may be implemented. For example, different types of end effectors may be employed. Also, where materials are disclosed for certain components, other materials may be used. The foregoing description and following claims are intended to cover all such modification and variations.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A surgical instrument comprising:
    a shaft assembly, comprising:
        an inner tube extending longitudinally along the shaft assembly;
        an outer tube coaxially aligned with the inner tube along a combined length of the inner tube and the outer tube;
        a phase change material continuously disposed along the combined length of the inner tube and the outer tube in an annular space defined between the inner tube and the outer tube, wherein the phase change material is transitionable between a flexible mode and a rigidized mode, wherein, in the flexible mode, the combined length is flexible to define a plurality of curved orientations, wherein, in the flexible mode, the inner tube and the outer tube are longitudinally movable relative to each other between a plurality of relative positions, wherein the phase change material, in the rigidized mode, maintains the plurality of curved orientations, and wherein the phase change material, in the rigidized mode, constrains relative longitudinal motion between the inner tube and the outer tube; and
        an activation link extending longitudinally along the combined length of the inner tube and outer tube, wherein the activation link at least partially extends through the phase change material in the annular space between the inner tube and the outer tube, and wherein the activation link is configured to transition the phase change material between the flexible mode and the rigidizable mode.

2. The surgical instrument of claim 1, further comprising:
    a source of activation energy; and
    an activation control member for selectively applying the activation energy to the activation link.

3. The surgical instrument of claim 1, wherein the phase change material comprises a solid phase and a non-solid phase, wherein the phase change material is in the rigidized mode in the solid phase, and wherein the phase change material bonds the inner tube to the outer tube in the solid phase.

4. The surgical instrument of claim 3, wherein the inner tube comprises an outer wall disposed along the combined length, wherein the outer tube comprises an inner wall disposed along the combined length, and wherein the inner wall and the outer wall are treated to increase friction between the phase change material, in the solid phase, and the inner wall and the outer wall.

5. The surgical instrument of claim 4, wherein the inner wall and the outer wall are treated by one of cleaning, etching, and exposure to a corona arc.

* * * * *